(12) United States Patent
Narimatsu et al.

(10) Patent No.: US 7,273,729 B2
(45) Date of Patent: Sep. 25, 2007

(54) CHONDROITIN SYNTHASE AND DNA ENCODING THE ENZYME

(75) Inventors: Hisashi Narimatsu, Tsukuba (JP); Koji Kimata, Nagoya (JP); Toshikazu Yada, Kuwana (JP); Takashi Sato, Tsukuba (JP); Masanori Goto, Tsukuba (JP)

(73) Assignees: Seikagaku Kogyo Kabushiki Kaisha, Tokyo (JP); National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/516,099

(22) PCT Filed: May 30, 2003

(86) PCT No.: PCT/JP03/06881

§ 371 (c)(1),
(2), (4) Date: Nov. 30, 2004

(87) PCT Pub. No.: WO03/102194

PCT Pub. Date: Dec. 11, 2003

(65) Prior Publication Data

US 2006/0052335 A1 Mar. 9, 2006

(30) Foreign Application Priority Data

May 31, 2002 (JP) .............................. 2002-160854
May 6, 2003 (JP) .............................. 2003-128343

(51) Int. Cl.
| | |
|---|---|
| C12N 9/10 | (2006.01) |
| C12N 15/00 | (2006.01) |
| C12N 5/02 | (2006.01) |
| C12P 21/06 | (2006.01) |
| C12P 19/42 | (2006.01) |
| C12P 19/04 | (2006.01) |
| C07H 21/04 | (2006.01) |

(52) U.S. Cl. ...................... 435/84; 435/69.1; 435/193; 435/101; 435/320.1; 435/325; 536/23.1; 536/23.2; 536/53; 514/54

(58) Field of Classification Search ............. 435/320.1, 435/325, 183, 41, 69.1
See application file for complete search history.

(56) References Cited

U.S. PATENT DOCUMENTS

| | | | | |
|---|---|---|---|---|
| 6,913,919 B2 * | 7/2005 | Botstein et al. | .......... | 435/252.3 |
| 6,930,170 B2 * | 8/2005 | Desnoyers et al. | .......... | 530/350 |
| 6,953,836 B2 * | 10/2005 | Desnoyers et al. | .......... | 530/350 |
| 2002/0103125 A1 | 8/2002 | Ashkenazi et al. | | |
| 2002/0123463 A1 | 9/2002 | Ashkenazi et al. | | |
| 2002/0132252 A1 | 9/2002 | Ashkenazi et al. | | |
| 2002/0142961 A1 | 10/2002 | Ashkenazi et al. | | |

FOREIGN PATENT DOCUMENTS

| | | |
|---|---|---|
| JP | 2003-199583 A | 7/2002 |
| WO | WO99/63088 A2 | 12/1999 |
| WO | WO 00/27437 A2 | 5/2000 |
| WO | PCT/US00/08439 * | 12/2000 |
| WO | WO 00/73454 A1 * | 12/2000 |
| WO | WP 01/80810 A2 | 11/2001 |

OTHER PUBLICATIONS

Strausberg et al., Generation of initial analysis of more than 15,000 full-length human and mouse cDNA sequences, PNAS., 99(26): 16899-16903, 2002.*

Strausberg et al., Generation and initial analysis of more than 15,000 full-length human and mouse cDNA sequences. PNAS., 2002, vol. 99 (26): 16899-16903.*

Kitagawa et al., Molecular cloning of a chondroitin polymerizing factor that coperates with the chondroitin synthase for chondroitin polymerization. JBC., 2003, vol. 278(27): 23666-23671, published on line Apr. 25, 2003.*

Kitagawa, H. et al, "Characterization of serum beta-glucuronyltransferase involved on chondroitin sulfate biosynthesis" Glycobiology, 1997, vol. 7 No. 7, pp. 905-911.

Rohmann, K. et al, "Two N-acetylgalactosaminyl-transferase are involved in the biosynthesis of chondroitin sulfate" Eur. J. Biochem., 1985 vol. 148, No. 3, pp. 463-469.

Kitagawa H. et al, "Molecualar cloning and expression of a human chondroitin synthase" J. Biol. Chem., 2001, vol. 276 No. 42, pp. 38721-38726.

De Angelis P. L. et al, "Indentification and molecular cloning of a chondroitin synthase from Pasteurella multocida type F" J. Biol. Chem, 2000,vol. 275 No. 31, pp. 24124-24129.

Uyama T. et al, "Molecular cloning and expression of human chondroitin N-acetylgalactosaminlytransferase: the key enzyme for chain initiation and elongation of chondroitin/dermatan sulfate on the protein linkage region tetrasaccharide chared by heparin/heparin sulfate" J. Biol. Chem., 2002, vol. 277 No. 11 pp. 8841-8846.

Gotoh M. et al, "Molecular cloning and characterization of a novel chondroitin sulfate glucuronyltransferase that transfers glucuronic acid to N-acetylagalactosamine" J. Biol. Chem, 2002 vol. 277 No. 41 pp. 38179-38188.

Gotoh M. et al, "Enzymatic synthesis if chondroitin with a novel chondroitin sulfate N-acetylgalactosaminlytransferase that transfers N-acetylgalactosamine to glucuronic acid in initiation and elongation of chondroitin sulfate synthesis" J. Biol. Chem. 2002, vol. 277 No. 41, pp. 38189-38196.

Sato T. et al. "Differential roles to two N-acetylgalactosaminlytransferases, CSGalNAcT-1, and a novel enzyme, CSGalNA-cT-2, Initiation and elongation in synthesis of chondroitin sulfate" J. Biol. Chem. 2003, vol. 278 No. 5 pp. 3063-3071.

(Continued)

Primary Examiner—Rebecca E. Prouty
Assistant Examiner—Ganapathirama Raghu
(74) Attorney, Agent, or Firm—Sughrue Mion Pllc.

(57) ABSTRACT

A human-derived novel chondroitin synthase, which is an enzyme for synthesizing a fundamental backbone of chondroitin and has both glucuronic acid transferase activity and N-acetylgalactosamine transferase activity.

8 Claims, 9 Drawing Sheets

OTHER PUBLICATIONS

R. L. Strausberg et al., "Homo sapiens chondroitin polymerizing factor, mRNA (cDNA clone MGC:13135 IMAGE:4128192), complete cds" (2002).

J. L. Funderburgh et al., "Chondroitin synthase (Fragment)" (2002) XP. 002334012.

Hiroshi Kitagawa et al., "Molecular Cloning of a Chondroitin Polymerizing Factor That Cooperates with Chondroitin Synthase for Chondroitin Polymerization" (2003) The Journal of Biological Chemistry, vol. 278, No. 26, pp. 23666-23670.

H. Kitagawa, Chondroitin sulfate synthase 2 (EC 2.4.1.175) (Glucuronosyl-N-acetylgalactosaminyl-proteoglycan 4-acetylgalactosaminyltransferease II)(N-acetylgalactosaminyl-proteoglycan 3-beta-glucuronosyltransfer (Chondroitin glucuronyltransferase II) (N-acetylgalactosaminyltransferase)(Chondroitin polymerizing) (2005).

Partial European Search Report dated Jul. 12, 2005.

* cited by examiner

SEQUENCE LISTING

```
<160> NUMBER OF SEQ ID NOS: 7

<210> SEQ ID NO 1
<211> LENGTH: 2328
<212> TYPE: DNA
<213> ORGANISM: Homo sapiens
<220> FEATURE:
<221> NAME/KEY: CDS
<222> LOCATION: (1)..(2328)

<400> SEQUENCE: 1 atg cgg gca tcg ctg ctg ctg tcg gtg ctg cgg ccc gca ggg ccc gtg      48
Met Arg Ala Ser Leu Leu Leu Ser Val Leu Arg Pro Ala Gly Pro Val
  1               5                  10                  15 gcc gtg ggc atc tcc ctg ggc ttc acc ctg agc ctc agc gtc acc          96
Ala Val Gly Ile Ser Leu Gly Phe Thr Leu Ser Leu Leu Ser Val Thr
              20                  25                  30 tgg gtg gag gag ccg tgc ggc cca ggc ccg ccc caa cct gga gac tct     144
Trp Val Glu Glu Pro Cys Gly Pro Gly Pro Pro Gln Pro Gly Asp Ser
          35                  40                  45 gag ctg ccg ccg cgc ggc aac acc aac gcg gcg cgc cgg ccc aac tcg     192
Glu Leu Pro Pro Arg Gly Asn Thr Asn Ala Ala Arg Arg Pro Asn Ser
      50                  55                  60 gtg cag ccc gga gcg gag cgc gag aag ccc ggg gcc ggc gaa ggc gcc     240
Val Gln Pro Gly Ala Glu Arg Glu Lys Pro Gly Ala Gly Glu Gly Ala
  65                  70                  75                  80 ggg gag aat tgg gag ccg cgc gtc ttg ccc tac cac cct gca cag ccc     288
Gly Glu Asn Trp Glu Pro Arg Val Leu Pro Tyr His Pro Ala Gln Pro
```

-continued

```
                         85                    90                    95
ggc cag gcc gcc aaa aag gcc gtc agg acc cgc tac atc agc acg gag        336
Gly Gln Ala Ala Lys Lys Ala Val Arg Thr Arg Tyr Ile Ser Thr Glu
                100                   105                   110 ctg ggc atc agg cag agg ctg ctg gtg gcg gtg ctg acc tct cag acc        384
Leu Gly Ile Arg Gln Arg Leu Leu Val Ala Val Leu Thr Ser Gln Thr
            115                   120                   125 acg ctg ccc acg ctg ggc gtg gcc gtg aac cgc acg ctg ggc cac cgg        432
Thr Leu Pro Thr Leu Gly Val Ala Val Asn Arg Thr Leu Gly His Arg
        130                   135                   140 ctg gag cgt gtg gtg ttc ctg acg ggc gca cgg ggc cgc cgg gcc cca        480
Leu Glu Arg Val Val Phe Leu Thr Gly Ala Arg Gly Arg Arg Ala Pro
    145                   150                   155                   160 cct ggc atg gca gtg gtg acg ctg ggc gag gag cga ccc att gga cac        528
Pro Gly Met Ala Val Val Thr Leu Gly Glu Glu Arg Pro Ile Gly His
                165                   170                   175 ctg cac ctg gcg ctg cgc cac ctg ctg gag cag cac ggc gac gac ttt        576
Leu His Leu Ala Leu Arg His Leu Leu Glu Gln His Gly Asp Asp Phe
            180                   185                   190 gac tgg ttc ttc ctg gtg cct gac acc acc tac acc gag gcg cac ggc        624
Asp Trp Phe Phe Leu Val Pro Asp Thr Thr Tyr Thr Glu Ala His Gly
        195                   200                   205 ctg gca cgc cta act ggc cac ctc agc ctg gcc tcc gcc gcc cac ctg        672
Leu Ala Arg Leu Thr Gly His Leu Ser Leu Ala Ser Ala Ala His Leu
    210                   215                   220 tac ctg ggc cgg ccc cag gac ttc atc ggc gga gag ccc acc ccc ggc        720
Tyr Leu Gly Arg Pro Gln Asp Phe Ile Gly Gly Glu Pro Thr Pro Gly
225                   230                   235                   240 cgc tac tgc cac gga ggc ttt ggg gtg ctg ctg tcg cgc atg ctg ctg        768
Arg Tyr Cys His Gly Gly Phe Gly Val Leu Leu Ser Arg Met Leu Leu
                245                   250                   255 caa caa ctg cgc ccc cac ctg gaa ggc tgc cgc aac gac atc gtc agt        816
Gln Gln Leu Arg Pro His Leu Glu Gly Cys Arg Asn Asp Ile Val Ser
            260                   265                   270 gcg cgc cct gac gag tgg ctg ggt cgc tgc att ctc gat gcc acc ggg        864
Ala Arg Pro Asp Glu Trp Leu Gly Arg Cys Ile Leu Asp Ala Thr Gly
        275                   280                   285 gtg ggc tgc act ggt gac cac gag ggg gtg cac tat agc cat ctg gag        912
Val Gly Cys Thr Gly Asp His Glu Gly Val His Tyr Ser His Leu Glu
    290                   295                   300 ctg agc cct ggg gag cca gtg cag gag ggg gac cct cat ttc cga agt        960
Leu Ser Pro Gly Glu Pro Val Gln Glu Gly Asp Pro His Phe Arg Ser
305                   310                   315                   320 gcc ctg aca gcc cac cct gtg cgt gac cct gtg cac atg tac cag ctg       1008
Ala Leu Thr Ala His Pro Val Arg Asp Pro Val His Met Tyr Gln Leu
                325                   330                   335 cac aaa gct ttc gcc cga gct gaa ctg gaa cgc acg tac cag gag atc       1056
His Lys Ala Phe Ala Arg Ala Glu Leu Glu Arg Thr Tyr Gln Glu Ile
            340                   345                   350 cag gag tta cag tgg gag atc cag aat acc agc cat ctg gcc gtt gat       1104
Gln Glu Leu Gln Trp Glu Ile Gln Asn Thr Ser His Leu Ala Val Asp
        355                   360                   365 ggg gac cgg gca gct gct tgg ccc gtg ggt att cca gca cca tcc cgc       1152
Gly Asp Arg Ala Ala Ala Trp Pro Val Gly Ile Pro Ala Pro Ser Arg
    370                   375                   380 ccg gcc tcc cgc ttt gag gtg ctg cgc tgg gac tac ttc acg gag cag       1200
Pro Ala Ser Arg Phe Glu Val Leu Arg Trp Asp Tyr Phe Thr Glu Gln
385                   390                   395                   400 cac gct ttc tcc tgc gcc gat ggc tca ccc cgc tgc cca ctg cgt ggg       1248
```

```
        His Ala Phe Ser Cys Ala Asp Gly Ser Pro Arg Cys Pro Leu Arg Gly
                    405                 410                 415 gct gac cgg gct gat gtg gcc gat gtt ctg ggg aca gct cta gag gag           1296
Ala Asp Arg Ala Asp Val Ala Asp Val Leu Gly Thr Ala Leu Glu Glu
            420                 425                 430 ctg aac cgc cgc tac cac ccg gcc ttg cgg ctc cag aag cag cag ctg           1344
Leu Asn Arg Arg Tyr His Pro Ala Leu Arg Leu Gln Lys Gln Gln Leu
            435                 440                 445 gtg aat ggc tac cga cgc ttt gat ccg gcc cgg ggt atg gaa tac acg           1392
Val Asn Gly Tyr Arg Arg Phe Asp Pro Ala Arg Gly Met Glu Tyr Thr
            450                 455                 460 ctg gac ttg cag ctg gag gca ctg acc ccc cag gga ggc cgc cgg ccc           1440
Leu Asp Leu Gln Leu Glu Ala Leu Thr Pro Gln Gly Gly Arg Arg Pro
465                 470                 475                 480 ctc act cgc cga gtg cag ctg ctc cgg ccg ctg agc cgc gtg gag atc           1488
Leu Thr Arg Arg Val Gln Leu Leu Arg Pro Leu Ser Arg Val Glu Ile
                    485                 490                 495 ttg cct gtg ccc tat gtc act gag gcc tca cgt ctc act gtg ctg ctg           1536
Leu Pro Val Pro Tyr Val Thr Glu Ala Ser Arg Leu Thr Val Leu Leu
                500                 505                 510 cct cta gct gcg gct gag cgt gac ctg gcc cct ggc ttc ttg gag gcc           1584
Pro Leu Ala Ala Ala Glu Arg Asp Leu Ala Pro Gly Phe Leu Glu Ala
            515                 520                 525 ttt gcc act gca gca ctg gag cct ggt gat gct gcg gca gcc ctg acc           1632
Phe Ala Thr Ala Ala Leu Glu Pro Gly Asp Ala Ala Ala Ala Leu Thr
            530                 535                 540 ctg ctg cta ctg tat gag ccg cgc cag gcc cag cgc gtg gcc cat gca           1680
Leu Leu Leu Leu Tyr Glu Pro Arg Gln Ala Gln Arg Val Ala His Ala
545                 550                 555                 560 gat gtc ttc gca cct gtc aag gcc cac gtg gca gag ctg gag cgg cgt           1728
Asp Val Phe Ala Pro Val Lys Ala His Val Ala Glu Leu Glu Arg Arg
                565                 570                 575 ttc ccc ggt gcc cgg gtg cca tgg ctc agt gtg cag aca gcc gca ccc           1776
Phe Pro Gly Ala Arg Val Pro Trp Leu Ser Val Gln Thr Ala Ala Pro
                580                 585                 590 tca cca ctg cgc ctc atg gat cta ctc tcc aag aag cac ccg ctg gac           1824
Ser Pro Leu Arg Leu Met Asp Leu Leu Ser Lys Lys His Pro Leu Asp
            595                 600                 605 aca ctg ttc ctg ctg gcc ggg cca gac acg gtg ctc acg cct gac ttc           1872
Thr Leu Phe Leu Leu Ala Gly Pro Asp Thr Val Leu Thr Pro Asp Phe
            610                 615                 620 ctg aac cgc tgc cgc atg cat gcc atc tcc ggc tgg cag gcc ttc ttt           1920
Leu Asn Arg Cys Arg Met His Ala Ile Ser Gly Trp Gln Ala Phe Phe
625                 630                 635                 640 ccc atg cat ttc caa gcc ttc cac cca gct gtg gcc cca caa ggg                1968
Pro Met His Phe Gln Ala Phe His Pro Ala Val Ala Pro Gln Gly
                645                 650                 655 cct ggg ccc cca gag ctg ggc cgt gac act ggc cgc ttt gat cgc cag           2016
Pro Gly Pro Pro Glu Leu Gly Arg Asp Thr Gly Arg Phe Asp Arg Gln
            660                 665                 670 gca gcc agc gag gcc tgc ttc tac aac tcc gac tac gtg gca gcc cgt           2064
Ala Ala Ser Glu Ala Cys Phe Tyr Asn Ser Asp Tyr Val Ala Ala Arg
            675                 680                 685 ggg cgc ctg gcg gca gcc tca gaa caa gaa gag gag ctg ctg gag agc           2112
Gly Arg Leu Ala Ala Ala Ser Glu Gln Glu Glu Glu Leu Leu Glu Ser
            690                 695                 700 ctg gat gtg tac gag ctg ttc ctc cac ttc tcc agt ctg cat gtg ctg           2160
Leu Asp Val Tyr Glu Leu Phe Leu His Phe Ser Ser Leu His Val Leu
705                 710                 715                 720
```

-continued

| | |
|---|---|
| cgg gcg gtg gag ccg gcg ctg ctg cag cgc tac cgg gcc cag acg tgc<br>Arg Ala Val Glu Pro Ala Leu Leu Gln Arg Tyr Arg Ala Gln Thr Cys<br>              725                                     730                      735 | 2208 |
| agc gcg agg ctc agt gag gac ctg tac cac cgc tgc ctc cag agc gtg<br>Ser Ala Arg Leu Ser Glu Asp Leu Tyr His Arg Cys Leu Gln Ser Val<br>        740                                745                                750 | 2256 |
| ctt gag ggc ctc ggc tcc cga acc cag ctg gcc atg cta ctc ttt gaa<br>Leu Glu Gly Leu Gly Ser Arg Thr Gln Leu Ala Met Leu Leu Phe Glu<br>755                                  760                                765 | 2304 |
| cag gag cag ggc aac agc acc tga<br>Gln Glu Gln Gly Asn Ser Thr<br>770                              775 | 2328 |

<210> SEQ ID NO 2
<211> LENGTH: 775
<212> TYPE: PRT
<213> ORGANISM: Homo sapiens

<400> SEQUENCE: 2

Met Arg Ala Ser Leu Leu Ser Val Leu Arg Pro Ala Gly Pro Val
1               5                   10                  15

Ala Val Gly Ile Ser Leu Gly Phe Thr Leu Ser Leu Leu Ser Val Thr
                20                  25                  30

Trp Val Glu Glu Pro Cys Gly Pro Gly Pro Pro Gln Pro Gly Asp Ser
            35                  40                  45

Glu Leu Pro Pro Arg Gly Asn Thr Asn Ala Ala Arg Arg Pro Asn Ser
        50                  55                  60

Val Gln Pro Gly Ala Glu Arg Glu Lys Pro Gly Ala Gly Glu Gly Ala
65                  70                  75                  80

Gly Glu Asn Trp Glu Pro Arg Val Leu Pro Tyr His Pro Ala Gln Pro
                85                  90                  95

Gly Gln Ala Ala Lys Lys Ala Val Arg Thr Arg Tyr Ile Ser Thr Glu
            100                 105                 110

Leu Gly Ile Arg Gln Arg Leu Leu Val Ala Val Leu Thr Ser Gln Thr
        115                 120                 125

Thr Leu Pro Thr Leu Gly Val Ala Val Asn Arg Thr Leu Gly His Arg
130                 135                 140

Leu Glu Arg Val Val Phe Leu Thr Gly Ala Arg Gly Arg Arg Ala Pro
145                 150                 155                 160

Pro Gly Met Ala Val Val Thr Leu Gly Glu Glu Arg Pro Ile Gly His
                165                 170                 175

Leu His Leu Ala Leu Arg His Leu Leu Glu Gln His Gly Asp Asp Phe
            180                 185                 190

Asp Trp Phe Phe Leu Val Pro Asp Thr Thr Tyr Thr Glu Ala His Gly
        195                 200                 205

Leu Ala Arg Leu Thr Gly His Leu Ser Leu Ala Ser Ala Ala His Leu
210                 215                 220

Tyr Leu Gly Arg Pro Gln Asp Phe Ile Gly Gly Pro Thr Pro Gly
225                 230                 235                 240

Arg Tyr Cys His Gly Gly Phe Gly Val Leu Leu Ser Arg Met Leu Leu
                245                 250                 255

Gln Gln Leu Arg Pro His Leu Glu Gly Cys Arg Asn Asp Ile Val Ser
            260                 265                 270

Ala Arg Pro Asp Glu Trp Leu Gly Arg Cys Ile Leu Asp Ala Thr Gly
        275                 280                 285

Val Gly Cys Thr Gly Asp His Glu Gly Val His Tyr Ser His Leu Glu

```
            290                 295                 300
Leu Ser Pro Gly Glu Pro Val Gln Glu Gly Asp Pro His Phe Arg Ser
305                 310                 315                 320

Ala Leu Thr Ala His Pro Val Arg Asp Pro Val His Met Tyr Gln Leu
                325                 330                 335

His Lys Ala Phe Ala Arg Ala Glu Leu Glu Arg Thr Tyr Gln Glu Ile
                340                 345                 350

Gln Glu Leu Gln Trp Glu Ile Gln Asn Thr Ser His Leu Ala Val Asp
                355                 360                 365

Gly Asp Arg Ala Ala Ala Trp Pro Val Gly Ile Pro Ala Pro Ser Arg
370                 375                 380

Pro Ala Ser Arg Phe Glu Val Leu Arg Trp Asp Tyr Phe Thr Glu Gln
385                 390                 395                 400

His Ala Phe Ser Cys Ala Asp Gly Ser Pro Arg Cys Pro Leu Arg Gly
                405                 410                 415

Ala Asp Arg Ala Asp Val Ala Asp Val Leu Gly Thr Ala Leu Glu Glu
                420                 425                 430

Leu Asn Arg Arg Tyr His Pro Ala Leu Arg Leu Gln Lys Gln Gln Leu
                435                 440                 445

Val Asn Gly Tyr Arg Arg Phe Asp Pro Ala Arg Gly Met Glu Tyr Thr
450                 455                 460

Leu Asp Leu Gln Leu Glu Ala Leu Thr Pro Gln Gly Arg Arg Pro
465                 470                 475                 480

Leu Thr Arg Arg Val Gln Leu Leu Arg Pro Leu Ser Arg Val Glu Ile
                485                 490                 495

Leu Pro Val Pro Tyr Val Thr Glu Ala Ser Arg Leu Thr Val Leu Leu
                500                 505                 510

Pro Leu Ala Ala Ala Glu Arg Asp Leu Ala Pro Gly Phe Leu Glu Ala
                515                 520                 525

Phe Ala Thr Ala Ala Leu Glu Pro Gly Asp Ala Ala Ala Leu Thr
530                 535                 540

Leu Leu Leu Leu Tyr Glu Pro Arg Gln Ala Gln Arg Val Ala His Ala
545                 550                 555                 560

Asp Val Phe Ala Pro Val Lys Ala His Val Ala Glu Leu Glu Arg Arg
                565                 570                 575

Phe Pro Gly Ala Arg Val Pro Trp Leu Ser Val Gln Thr Ala Ala Pro
                580                 585                 590

Ser Pro Leu Arg Leu Met Asp Leu Leu Ser Lys Lys His Pro Leu Asp
                595                 600                 605

Thr Leu Phe Leu Leu Ala Gly Pro Asp Thr Val Leu Thr Pro Asp Phe
610                 615                 620

Leu Asn Arg Cys Arg Met His Ala Ile Ser Gly Trp Gln Ala Phe Phe
625                 630                 635                 640

Pro Met His Phe Gln Ala Phe His Pro Ala Val Ala Pro Gln Gly
                645                 650                 655

Pro Gly Pro Pro Glu Leu Gly Arg Asp Thr Gly Arg Phe Asp Arg Gln
                660                 665                 670

Ala Ala Ser Glu Ala Cys Phe Tyr Asn Ser Asp Tyr Val Ala Ala Arg
                675                 680                 685

Gly Arg Leu Ala Ala Ala Ser Glu Gln Glu Glu Leu Leu Glu Ser
                690                 695                 700

Leu Asp Val Tyr Glu Leu Phe Leu His Phe Ser Ser Leu His Val Leu
705                 710                 715                 720
```

```
Arg Ala Val Glu Pro Ala Leu Leu Gln Arg Tyr Arg Ala Gln Thr Cys
            725                 730                 735

Ser Ala Arg Leu Ser Glu Asp Leu Tyr His Arg Cys Leu Gln Ser Val
        740                 745                 750

Leu Glu Gly Leu Gly Ser Arg Thr Gln Leu Ala Met Leu Leu Phe Glu
            755                 760                 765

Gln Glu Gln Gly Asn Ser Thr
    770                 775

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: 5' primer
      for PCR

<400> SEQUENCE: 3
ggaattccgg ccaggccgcc aaaaaggc                                    28

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: 3' primer
      for PCR

<400> SEQUENCE: 4
cgggatcctc aggtgctgtt gccctgctcc                                  30

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: 5' primer
      for RT-PCR

<400> SEQUENCE: 5
gctgaactgg aacgcacgta                                             20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: 3' primer
      for RT-PCR

<400> SEQUENCE: 6
cgggatggtg ctggaatac                                              19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: probe for
      RT-PCR

<400> SEQUENCE: 7
agatccagga gttacagtgg                                             20
```

CHONDROITIN SYNTHASE AND DNA ENCODING THE ENZYME

TECHNICAL FIELD

The present invention relates to an enzyme which synthesizes a sugar chain backbone of chondroitin/chondroitin sulfate (fundamental backbone: hereinafter also referred to as "chondroitin backbone") and a DNA encoding the enzyme. More particularly, the present invention relates to an enzyme which transfers a D-glucuronic acid residue to an N-acetyl-D-galactosamine residue when the N-acetyl-D-galactosamine residue is present at the non-reducing end of the chondroitin backbone, or transfers an N-acetyl-D-galactosamine residue to a D-glucuronic acid residue when the D-glucuronic acid residue is present at the non-reducing end, and a DNA encoding the enzyme.

BACKGROUND OF THE INVENTION

In the present specification, regarding sugars and sugar residues as used herein, all optical isomers are D-isomers, unless otherwise indicated.

Chondroitin sulfate and chondroitin are kinds of glycosaminoglycans having, as the fundamental backbone, a repeating structure of a disaccharide of a D-glucuronic acid residue (hereinafter sometimes simply referred to as "glucuronic acid" or "GlcUA") and an N-acetyl-D-galactosamine residue (hereinafter sometimes simply referred to as "N-acetyl-galactosamine" or "GalNAc") (i.e., -[GlcUAβ(1,3)-GalNAcβ(1,4)-]$_n$; n is an integer of 2 or more).

Until now, glycosaminoglycans, particularly chondroitin and chondroitin sulfate, have been extracted and purified from cartilages, organs and the like in animals. However, due to shortage of the materials, a method for artificially synthesizing a chondroitin backbone common to chondroitin and chondroitin sulfate has been recently studied. Particularly, a method using a human-derived enzyme is preferred since a bio-defense mechanism such as an antigen-antibody reaction does not strongly occur even when the artificially synthesized chondroitin or chondroitin sulfate is contaminated with the enzyme. At present, only one enzyme is known as the enzyme for synthesizing such a chondroitin backbone, particularly an enzyme which is derived from human and has both GlcUA transferring activity and GalNAc transferring activity (*J. Biol. Chem.*, 276, 38721-38726 (2001)).

It is considered that use of a cocktail system containing several types of enzymes is preferred for the synthesis of the chondroitin backbone. This is because the different optimum reaction conditions of respective enzymes can relax the reaction conditions of the general reaction system. However, only the above-described enzyme is known at present as an enzyme which is derived from human and has both GlcUA transferring activity and GalNAc transferring activity, and it is the present situation that studies on the synthesis of the chondroitin backbone are insufficient because of the difficulty in strictly controlling the conditions.

Accordingly, a human-derived novel enzyme which is an enzyme for synthesizing a chondroitin backbone and has both GlcUA transferring activity and GalNAc transferring activity has been desired.

DISCLOSURE OF THE INVENTION

The present invention relates to the following (1) to (14).

(1) A chondroitin synthase which consists of a polypeptide consisting of the amino-acid sequence represented by SEQ ID NO:2 or an amino acid sequence consisting of amino acid numbers 97 to 755 in the amino acid sequence represented by SEQ ID NO:2, or a sugar chain-bound polypeptide in which a sugar chain is bound to the polypeptide.

(2) A chondroitin synthase comprising a polypeptide which has enzyme activity of transferring an N-acetyl-D-galactosamine residue to an N-acetyl-D-galactosamine acceptor or enzyme activity of transferring a D-glucuronic acid residue to a D-glucuronic acid acceptor, and consists of an amino acid sequence having substitution, deletion, insertion, addition and/or transposition of 1 to 131 amino acid residues in an amino acid sequence consisting of amino acid numbers 97 to 755 in the amino acid sequence represented by SEQ ID NO:2.

(3) The chondroitin synthase according to (2), which has enzyme activity of transferring an N-acetyl-D-galactosamine residue from an N-acetyl-D-galactosamine donor to a D-glucuronic acid residue of chondroitin having the D-glucuronic acid residue at the non-reducing end, and has enzyme activity of transferring a D-glucuronic acid residue from a D-glucuronic acid donor to an N-acetyl-D-galactosamine residue of chondroitin having the N-acetyl-galactosamine residue at the non-reducing end.

(4) A nucleic acid encoding the chondroitin synthase according to any one of (1) to (3).

(5) An expression vector which comprises the nucleic acid according to (4).

(6) The expression vector according to (5), which is capable of being expressed in a eucaryotic cell.

(7) A transformant which comprises the expression vector according to (5) or (6).

(8) A process for producing a chondroitin synthase, which comprises growing the transformant according to (7) to produce and accumulate a chondroitin synthase as a grown material, and recovering the chondroitin synthase from the grown material.

(9) A method for synthesizing a sugar chain having a structure represented by the following formula (2), which comprises allowing the chondroitin synthase according to any one of (1) to (3) to act on an N-acetyl-D-galactosamine acceptor having a structure represented by the following formula (1) and an N-acetyl-D-galactosamine donor to thereby transfer an N-acetyl-D-galactosamine residue to the N-acetyl-D-galactosamine acceptor:

(GlcUA-GalNAc)$_n$-(GlcUA)$_m$ (1)

GalNAc-(GlcUA-GalNAc)$_n$-(GlcUA)$_m$ (2)

wherein, in formulae (1) and (2), GalNAc represents the N-acetyl-D-galactosamine residue; GlcUA represents a D-glucuronic acid residue; n is an integer of 1 or more; m is 1 or 0; and — represents a glycoside bond.

(10) A method for synthesizing a sugar chain having a structure represented by the following formula (4), which comprises allowing the chondroitin synthase according to any one of (1) to (3) to act upon a D-glucuronic acid acceptor having a structure represented by the following formula (3) and a D-glucuronic acid donor to thereby transfer a D-glucuronic acid residue to the D-glucuronic acid acceptor:

$$(GalNAc\text{-}GlcUA)_n\text{-}(GalNAc)_m \quad (3)$$

$$GlcUA\text{-}(GalNAc\text{-}GlcUA)_n\text{-}(GalNAc)_m \quad (4)$$

wherein, in formulae (3) and (4), GalNAc represents an N-acetyl-D-galactosamine residue; GlcUA represents the D-glucuronic acid residue; n is an integer of 1 or more; m is 1 or 0; and —represents a glycoside bond.

(11) Use of the chondroitin synthase according to any one of (1) to (3) for synthesis of a sugar chain having a structure represented by the following formula (2) by transferring an N-acetyl-D-galactosamine residue to a D-glucuronic acid residue which is present at the non-reducing end of an N-acetyl-D-galactosamine acceptor having a structure represented by the following formula (1):

$$(GlcUA\text{-}GalNAc)_n\text{-}(GlcUA)_m \quad (1)$$

$$GalNAc\text{-}(GlcUA\text{-}GalNAc)_n\text{-}(GlcUA)_m \quad (2)$$

wherein, in formulae (1) and (2), GalNAc represents the N-acetyl-D-galactosamine residue; GlcUA represents a D-glucuronic acid residue; n is an integer of 1 or more; m is 1 or 0; and —represents a glycoside bond.

(12) Use of the chondroitin synthase according to any one of (1) to (3) for synthesis of a sugar chain having a structure represented by the following formula (4) by transferring a D-glucuronic acid residue to an N-acetyl-galactosamine residue which is present at the non-reducing end of a D-glucuronic acid acceptor having a structure represented by the following formula (3):

$$(GalNAc\text{-}GlcUA)_n\text{-}(GalNAc)_m \quad (3)$$

$$GlcUA\text{-}(GalNAc\text{-}GlcUA)_n\text{-}(GalNAc)_m \quad (4)$$

wherein, in formulae (3) and (4), GalNAc represents an N-acetyl-D-galactosamine residue; GlcUA represents the D-glucuronic acid residue; n is an integer of 1 or more; m is 1 or 0; and —represents a glycoside bond.

(13) An activity-controlling agent of the chondroitin synthase according to any one of (1) to (3).

(14) An agent for treating diseases caused by a change in activity of the chondroitin synthase according to any one of (1) to (3), which comprises the activity-controlling agent according to (13) as an active ingredient.

BEST MODE FOR CARRYING OUT THE INVENTION

Figure 1:
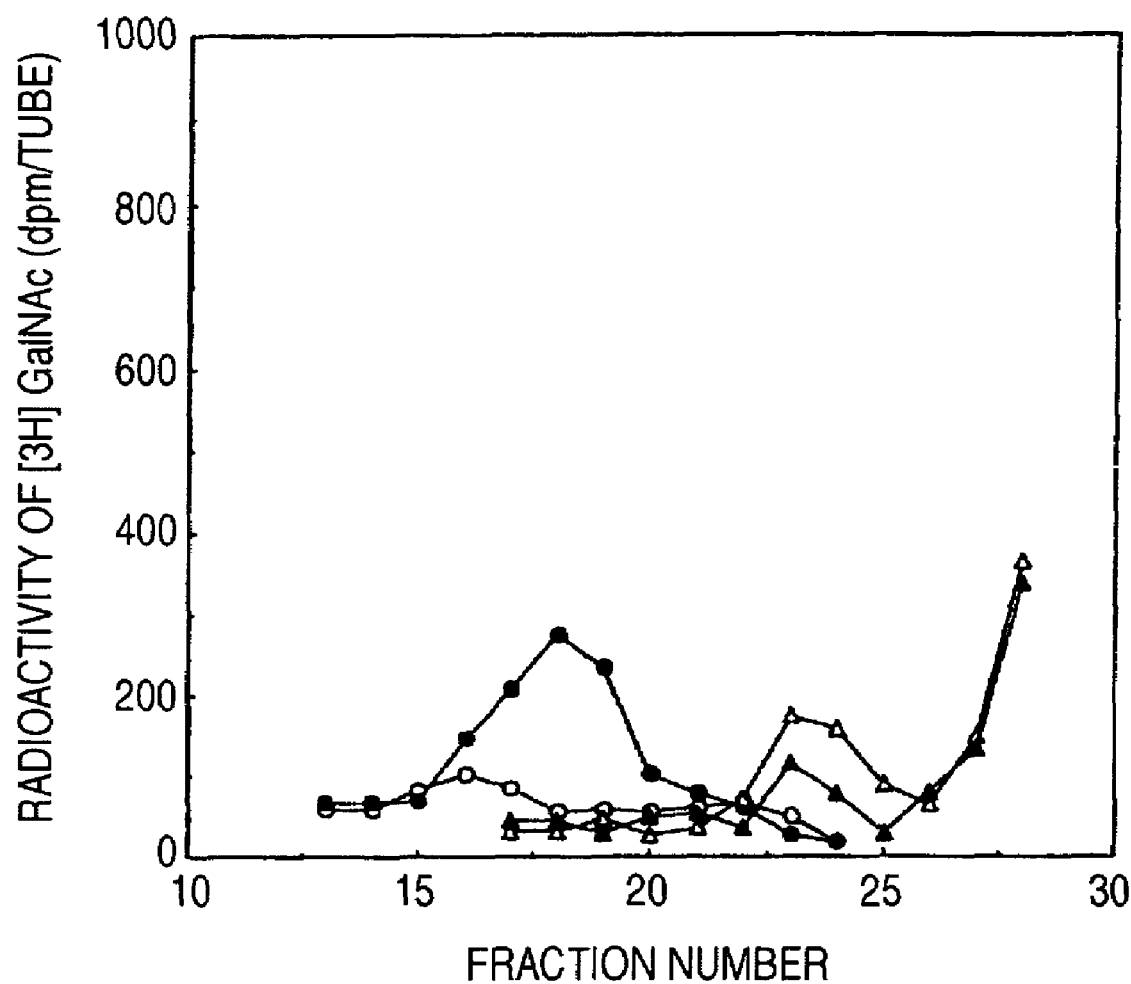
FIG. 1 is a graph showing a chromatography chart which shows synthesis of odd-numbered saccharides by the GalNAc transfer activity of the enzyme of the present invention. Open circles represent a chart showing the GalNAc transfer activity upon chondroitin sulfate, closed circles represent chart showing the GalNAc transfer activity upon chondroitin, open triangles represent a chart showing the GalNAc transfer activity upon chondroitin sulfate deca-saccharide, and closed triangles represent a chart showing the GalNAc transfer activity upon chondroitin deca-saccharide.

In order to solve the above-described problems, the present inventors have conducted intensive studies, and found, as a result, that there is a different enzyme having an enzyme activity similar to that of the conventionally known chondroitin synthase. Thereafter, the present invention has been accomplished by obtaining a DNA for the enzyme and preparing the enzyme.

The present invention is described below in detail based on the embodiments of the present invention.

(1) Enzyme of the Present Invention

The enzyme of the present invention is a chondroitin synthase which consists of a polypeptide consisting of the amino acid sequence represented by SEQ ID NO:2 or an amino acid sequence consisting of amino acid numbers 97 to 755 in the amino acid sequence represented by SEQ ID NO:2, or a sugar chain-bound polypeptide in which a sugar chain is bound to the polypeptide.

The enzyme of the present invention has activity of transferring a GalNAc residue and activity of transferring a GlcUA residue (the activity of transferring a GalNAc residue is referred to as "GalNAc transferring activity", and the activity of transferring a GlcUA residue is referred to as "GlcUA transferring activity") to sugar residues which are present at the non-reducing end of the chondroitin backbone. That is, the enzyme of the present invention shows the activity of transferring GalNAc to a GlcUA residue when the GlcUA residue is present at the non-reducing end of the chondroitin backbone, and shows the activity of transferring GlcUA to a GalNAc residue when the GalNAc residue is present at the non-reducing end. This is because such an enzyme has the most valuable in synthesizing the chondroitin backbone.

Accordingly, it is preferred that the enzyme of the present invention uses both of a GalNAc acceptor having a GlcUA residue at the non-reducing end of the chondroitin backbone and a GlcUA acceptor having a GalNAc residue at the non-reducing end, as the sugar residue acceptors.

The GalNAc acceptor of the enzyme of the present invention comprises, for example, a structure represented by the following formula (1):

(GlcUA-GalNAc)$_n$-(GlcUA)$_m$                    (1)

In formula (1), GlcUA represents a D-glucuronic acid residue; GalNAc represents an N-acetyl-D-galactosamine residue; n is an integer of 1 or more; m is 1 or 0; and—represents a glycoside bond. In the GalNAc acceptor, the above-described n is preferably 2 or more, and more preferably 4 or more. This is because the chondroitin backbone can be efficiently elongated when it is within such arrange.

Examples of the GalNAc acceptor having the structure of formula (1) include chondroitin, chondroitin sulfate, and a molecular weight-lowered chondroitin or chondroitin sulfate obtained by digesting them, although not limited thereto.

The enzyme of the present invention transfers a GalNAc residue from a GalNAc donor to the GalNAc acceptor having the structure of formula (1). Since the enzyme of the present invention is useful in synthesizing the chondroitin backbone, it is preferred that the GalNAc residue is transferred to a GlcUA residue at the non-reducing end through a β1,4-glycoside bond.

The GalNAc donor is preferably a sugar nucleotide having the GalNAc residue. Examples of such a substance include adenosine diphosphate-N-acetylgalactosamine (ADP-GalNAc), uridine diphosphate-N-acetylgalactosamine (UDP-GalNAc), guanosine diphosphate-N-acetylgalactosamine (GDP-GalNAc), cytidine diphosphate-N-acetylgalactosamine (CDP-GalNAc) and the like, and UDP-GalNAc is most preferable. This is because UDP-GalNAc mainly acts as a GalNAc donor substrate in the in vivo synthesis of the chondroitin backbone. However, regarding the GalNAc transferring activity by the enzyme of the present invention, the GalNAc donor is not particularly limited, so long as it can provide a GalNAc residue.

A sugar chain having a structure represented by the following formula (2) is obtained when a GalNAc residue is transferred by the enzyme of the present invention to a GalNAc acceptor having a structure represented by the above-described formula (I):

GalNAc-(GlcUA-GalNAc)$_n$-(GlcUA)$_m$                    (2)

In formula (2), GlcUA, GalNAc, n, m and—have the same meanings as described above.

The GalNAc acceptor has a structure represented by the above-described formula (1), and a substance having a structure in which a sugar chain, a protein, a lipid, a synthetic high molecular weight compound or the like is further bound thereto can also be used as a GalNAc acceptor. When a GalNAc residue is transferred to the GalNAc acceptor, a compound having a structure represented by the above-described formula (2) and also having a sugar chain, a protein, a lipid, a synthetic high molecular weight compound or the like at the reducing end is obtained.

The GalNAc transferring activity of the enzyme of the present invention an be easily detected and measured by using a technique in which GalNAc is labeled with a radioisotope like the method described in Example 2(1) of this specification.

The GlcUA acceptor of the enzyme of the present invention comprises, for example, a structure represented by the following formula (3):

(GalNAc-GlcUA)$_n$-(GalNAc)$_m$                    (3)

In formula (1), GlcUA represents a D-glucuronic acid residue; GalNAc represents N-acetyl-D-galactosamine residue; n is an integer of 1 or more; m is 1 or 0; and—represents a glycoside bond. In the GlcUA acceptor, the above-described n is preferably 2 or more, and more preferably 4 or more. This is because the chondroitin backbone can be efficiently elongated when it is within such a range.

The enzyme of the present invention transfers GlcUA from a GlcUA donor to the GlcUA acceptor having the structure represented by formula (3). Since the enzyme of the present invention is useful in synthesizing the chondroitin backbone, it is preferred that the GlcUA residue is transferred to the GalNAc residue through a β1,3 glycoside bond.

The GlcUA donor is preferably a sugar nucleotide having a GlcUA residue. Examples of such a substance include adenosine diphosphate-N-glucuronic acid (ADP-GlcUA), uridine diphosphate-N-glucuronic acid (DP-GlcUA), guanosine diphosphate-N-glucuronic acid (GDP-GlcUA), cytidine diphosphate-N-glucuronic acid (CDP-GlcUA) and the like, and UDP-GlcUA is most preferable. This is because UDP-GlcUA mainly acts as a GlcUA donor in the in vivo synthesis of the chondroitin backbone. However, regarding GlcUA transferring activity by the enzyme of the present invention, the GlcUA donor is not particularly limited, so long as it can provide the GlcUA residue.

A sugar chain having a structure of the following formula (4) is obtained when a GlcUA residue is transferred by the enzyme of the present invention to a GlcUA acceptor having a structure represented by the above-described formula (3):

GlcUA-(GalNAc-GlcUA)$_n$-(GalNAc)$_m$                    (4)

In formula (4), GlcUA, GalNAc, n, m and—have the same meanings as described above.

Also, the GlcUA acceptor has a structure represented by the above-described formula (3), and a substance having a structure in which a sugar chain, a protein, a lipid, a synthetic high molecular weight compound or the like is further bound thereto can also be used as a GlcUA acceptor. When a GlcUA residue is transferred to such a GlcUA acceptor, a compound having a structure represented by the above-described formula (4) and also having a sugar chain, a protein, a lipid, a synthetic high molecular weight compound or the like at the reducing end is obtained.

The GlcUA transferring activity of the enzyme of the present invention can be easily measured by using a technique in which GlcUA is labeled with a radioisotope like the method described in Example 2(2) of this specification.

Preferably, the enzyme of the present invention comprises a polypeptide consisting of an amino acid sequence consisting of amino acid numbers 97 to 755 in the amino acid sequence represented by SEQ ID NO:2. This is because a polypeptide comprising an amino acid sequence of such a range has both of the above-described GalNAc transferring activity and GlcUA transferring activity (cf. Example 2 of this specification).

In general, the activity of an enzyme is maintained even when its constituting protein has a few substitution, deletion, insertion, addition and/or transposition of amino acids (hereinafter generally referred to as "amino acid mutation"), and an enzyme having such an amino acid mutation is called variant. In general, the enzyme activity is sufficiently maintained when the amino acid mutation is about 20% of the total number of amino acids, so long as it is not a mutation relating to the active center. Accordingly, so long as it has the above-described GalNAc transferring activity and GlcUA transferring activity, the enzyme of the present invention may also have a few amino acid mutation in the amino acid sequence consisting of amino acid numbers 97 to 755 in the amino acid sequence represented by SEQ ID NO:2 (it is possible to examine the presence or absence of the enzyme activity in accordance with Example 2 of this specification as described above). Also, the above-described "a few" is 20% or less of the total number of amino acids constituting the enzyme (131 or less in the case of the polypeptide consisting of amino acid numbers 97 to 755 in SEQ ID NO:2, namely a homology of 80% or more), preferably 15% or less (98 or less in the case of the polypeptide consisting of amino acid numbers 97 to 755 in SEQ ID NO:2, namely a homology of 85% or more), and most preferably 10% or less (65 or less in the case of the polypeptide consisting of amino acid numbers 97 to 755 in SEQ ID NO:2, namely a homology of 90% or more). The homology of the amino acid sequences can be easily calculated by using conventionally known computer software such as FASTA. The computer software such as FASTA is also served by internet.

Furthermore, it can be said that an enzyme constituted by a polypeptide consisting of the complete sequence of the amino acid sequence represented by SEQ ID NO:2 is also constituted by a polypeptide obtained through a few mutation generated in the polypeptide consisting of amino acid numbers 97 to 755, and it can be said that this is within the range of a preferable polypeptide as the enzyme of the present invention.

In addition, there are many mammal-derived proteins to which sugar chains are bound, and both of the enzyme consisting of the polypeptide alone and the enzyme in which sugar chain is bound to the polypeptide are included in the enzyme of the present invention.

Also, it is preferred that the enzyme of the present invention has the following properties.

Increase of the Activity:

The activity is increased when 10 mmol/l of a divalent metal cation preferably manganese ion or cobalt ion) is present in the reaction system. Specifically, a halide (such as chloride) of the above metal cation may be present in the reaction system.

Inhibition of the Activity:

The enzyme activity is substantially lost when 10 mmol/l in concentration of ethylenediaminetetraacetic acid is present in the reaction system;

Optimum Reaction pH:

The GlcUA transferring enzyme activity is from pH 5.7 to 6.7, preferably from pH 6.0 to 6.5, in a 2-morpholinoethanesulfonate (MES) buffer, and the GalNAc transferring enzyme activity is from pH 5.7 to 6.7, preferably from pH 6.0 to 6.4, in an MES buffer.

In addition, by making use of an activity measuring system of the enzyme of the present invention, a substance having activity of accelerating or inhibiting the enzyme activity can be obtained through its screening. It is possible to use such a substance as the active ingredient of an activity-controlling agent for the enzyme of the present invention. Furthermore, the activity-controlling agent can be used as an agent for treating diseases caused by a change in activity of the enzyme of the present invention.

(2) Nucleic Acid of the Present Invention

The nucleic acid of the present invention is characterized in that it encodes the enzyme of the present invention.

That is, the nucleic acid of the present invention is not particularly limited, so long as the enzyme of the present invention can be produced by a transformant transformed with an expression vector containing the nucleic acid or nucleic acid having a nucleotide sequence complementary thereto. Also, the nucleic acid of the present invention may be either a DNA or an RNA, but a DNA is preferred since it is markedly excellent in stability.

The preferred embodiments of the nucleic acid of the present invention include a DNA consisting of nucleotide numbers 289 to 2328 in the nucleotide sequence represented by SEQ ID NO:1, and a DNA consisting of the complete nucleotide sequence represented by SEQ ID NO:1.

By the way, in the biosynthesis of a protein, the genetic code (triplet) and the amino acid is not always 1:1, and there are cases in which the same amino acid corresponds to different triplets (degeneracy of genetic code). Accordingly, it can be easily understood by those skilled in the art that nucleic acid other than the exemplified specific nucleotide sequence, which contains other triplet corresponding to the same amino acid due to the degeneracy of genetic code, can also be used for obtaining the same enzyme of the present invention as a result, and it goes without saying that such nucleic acid is included in the nucleic acid of the present invention.

Nucleic acid which hybridizes with a DNA consisting of the nucleotide numbers 289 to 2328 in the nucleotide sequence represented by SEQ ID NO:1 or a DNA consisting of a nucleotide sequence complementary thereto under stringent conditions can be used, for example, as a probe for inspecting in vivo expression state and the like of the nucleic acid of the present invention, and is markedly useful as a reagent. Since the nucleic acid as a probe becomes difficult to handle when its molecular weight is too large, the molecular weight is, for example, 500 bp to 10 kbp, more preferably from 600 bp to 9 kbp, and most preferably from 700 bp to 8 kbp.

In this connection, the stringent conditions as used herein include conditions used in general hybridization techniques (e.g., Northern blot hybridization and Southern blot hybridization), and preferred conditions are conditions at 42° C. in the presence of 37.5% formamide, 5×SSPE (sodium chloride/sodium phosphate/EDTA (ethylenediaminetetraacetic acid) buffer), 5×Denhardt's solution and 0.5% SDS (sodium dodecyl sulfate).

(3) Expression Vector of the Present Invention

The expression vector of the present invention is an expression vector which comprises the nucleic acid of the present invention. In the expression vector of the present invention, regions relating to the gene expression (promoter region, enhancer region, operator region, etc.) are appropriately arranged so that the above-described nucleic acid of the present invention can be expressed in a host cell of interest, and the vector is constructed in such a manner that the nucleic acid of the present invention can be expressed suitably. Accordingly, a transformat can be obtained by introducing the expression vector of the present invention into an appropriate host cell. A basal vector of the expression vector of the present invention (a vector before transferring the gene of the present invention) is optionally selected in relation to the host cell into which the expression vector is introduced. For example, a vector for eucaryotic cell is selected as the basal vector when a eucaryotic cell (mammal cell, yeast, insect cell, etc.) is used as the host cell, and a vector for procaryotic cell is selected as the basal vector when a procaryotic cell (*Escherichia colt, Bacillus subtilis*, etc.) is used as the host cell. By the way, since the enzyme of the present invention is an enzyme derived from human, it is considered that an enzyme of the present invention having properties close to the natural counterpart (e.g., sugar chain-added embodiment, etc.) can be obtained when a eucaryotic cell is used in the present invention as the host cell. Accordingly, a eucaryotic cell, particularly a mammal cell, is preferably selected as the host cell, and a vector for eucaryotic cell, particularly a vector for mammal cell, is preferably selected as the basal vector of the expression vector of the present invention.

In this connection, techniques have been established in recent years as genetic engineering techniques in which a transformant is cultured or grown, and the substance of interest is isolated and purified from the culture or the grown material. It is preferable to construct the expression vector of the present invention in such a manner that isolation, purification and detection of the enzyme of the present invention become easy. Particularly, it is preferable to prepare the enzyme of the present invention by means of genetic engineering using the vector of the present invention constructed in such a manner that the enzyme of the present invention is expressed as a fusion protein with a marker peptide, because its isolation and purification become relatively easy.

Examples of the above-described marker peptide include a peptide which makes secretion, isolation, purification or detection of the protein of interest from the grown material of a transformant easy, by expressing as a fusion protein in which the peptide is bound to the protein of interest, in preparing the protein of interest through genetic recombination. Examples of the marker peptide include peptides such as a signal peptide (peptide consisting of 15 to 30 amino acid residues, which is present at the N-terminus of various proteins and functions inside the cells in the intracellular membrane permeation mechanism for the selection of protein; e.g., OmpA, OmpT, Dsb, etc.), protein kinase A, protein A (protein as a constituting component of the cell wall of *Staphylococcus aureus*, having a molecular weight of about 42,000), glutathione S transferase, His tag (sequence in which 6 to 10 histidine residues are arranged), myc tag (cMyc protein-derived sequence of 13 amino acid residues), FLAG peptide (a marker for analysis, consisting of 8 amino acid residues), T7 tag (consisting of the fiat 11 amino acid residues of gene 10 protein), S tag (consisting of 15 amino acid residues derived from pancreatic RNase A), HSV tag, pelB (a sequence of 22 amino acid residues of *Escherichia coli* outer membrane protein pelB), HA tag (consisting of 10 amino acid residues derived from hemagglutinin), Trx tag (thioredoxin sequence), CBP tag (calmodulin binding peptide), CBD tag (cellulose binding domain), CBR tag (collagen binding domain), β-lac/blu (β-lactamase), β-gal (β-galactosidase), luc (luciferase), HP-Thio (His-patch thioredoxin), HSP (heat shock peptide), Lnγ (laminin γ peptide), Fn (fibronectin partial peptide), GFP (green fluorescent peptide), YFP (yellow fluorescent peptide), CFP (cyan fluorescent peptide), BFP (blue fluorescent peptide), DsRed, DsRed2 (red fluorescent peptide), MBP (maltose binding peptide), LacZ (lactose operator), IgG (immunoglobulin G), avidin, and protein G, and any one of these marker peptides can be used. Among these, a signal peptide, protein kinase A, protein A, glutathione S transferase, His tag, myc tag, FLAG peptide, T7 tag, S tag, HSV tag, pelB or HA tag is preferred since it facilitates expression of the substance of the present invention by means of genetic engineering techniques and its purification, and it is particularly preferable to prepare the enzyme of the present invention as a fusion protein with FLAG peptide because of the markedly excellent handling.

Examples of the basal vector which can be expressed in mammal cells and can provide the enzyme of the present invention as a fusion protein with the above-described FLAG peptide include pFLAG-CMV-1 (manufactured by Sigma) and the like, but it is possible for those skilled in the art to select a suitable basal vector by judging from the host cell, the restriction enzyme, the marker peptide and the like used in the expression of the enzyme of the present invention.

(4) Processes for Preparing the Nucleic Acid of the Present Invention, the Expression Vector of the Present Invention and the Transformant Since the nucleotide sequence of the nucleic acid of the present invention has been disclosed by the present invention, it is possible for those skilled in the art to prepare optional primers based on the nucleotide sequences of both termini of a region of the nucleic acid of the present invention of interest or nucleic acid to be prepared, and to prepare the region of interest by amplifying it by PCR or the like using the primers. A DNA consisting of nucleotide numbers 289 to 2328 of SEQ ID NO:1 as a preferred embodiment of the nucleic acid of the present invention can be prepared as follows.

A partial sequence of the nucleic acid of the present invention can be obtained by carrying out BLAST search using the amino acid sequence of CSGlcA-T (amino acid sequence encoded by GenBank accession No. AB037823) as a query. Thereafter, the genomic sequence can be searched from a data base, for example, based on the EST obtained thereby (GenBank accession No. MN_018590, etc.). The genomic sequence can be searched by using, for example, GenScan (Stanford University, USA) or the like. The total nucleotide sequence represented by SEQ ID NO:1 can be obtained by this method. The DNA consisting of nucleotide numbers 289 to 2328 can be prepared by preparing primers from the nucleotide sequence obtained in this manner. As the preparation method of DNA, for example, a polymerase chain reaction method (hereinafter referred to as "PCR method") can be preferably cited. In the PCR method, it is preferred that appropriate restriction enzyme sites are contained in respective primers in advance corresponding to a vector, for facilitating introduction of the nucleic acid of the present invention into the vector. Examples of the primers include the nucleotide sequence represented by SEQ ID NO:3 (containing EcoRI site) as a 5' primer, and the nucleotide sequence represented by SEQ ID NO:4 (containing BamHI site) as a 3' primer.

For example, it can be found from the information of a data base that the genome obtained by the search based on the EST of GenBank accession No. MN_018590 by Gen-Scan is expressed in the human brain. Accordingly, a commercially available human brain cDNA library (e.g., Marathon-Ready cDNA human brain (manufactured by Clontech, etc.)) or the like can be used as the template of the PCR method.

When the PCR method is carried out by using the primers exemplified above, the nucleic acid of the present invention (DNA) is formed as an amplified product of about 2 kb. The amplified product can be isolated in accordance with the usual methods, for example, separation of DNA based on molecular weight such as agarose gel electrophoresis, cutting out of the gel, and extraction of the nucleic acid of the present invention.

Since the primers exemplified above contains EcoRI site and BamHI site, insertion into a vector having EcoRI and BamHI sites can be carried out in the usual way by treating with these restriction enzymes. For example, since the pFLAG-CMV-1 as a basal vector exemplified above contains EcoRI and BamHI sites, the vector of the present invention can be obtained by digesting this basal vector with EcoRI and BamHI and ligating it with the nucleic acid of the present invention.

The vector of the present invention can be introduced into a host cell in accordance with a usual method. When pFLAG-CMV-1 is used as the basal vector, a transformant can be obtained by introducing it into a mammal-derived cell, such as COS1 cell or COS7 cell, which functions as a host cell of pFLAG-CMV-1, according to a usual method such as electroporation.

(5) Preparation Method of the Enzyme of the Present Invention

The preparation method of the enzyme of the present invention is characterized in that the transformant of the present invention is grown, the enzyme of the present invention is accumulated in the grown material, and then the above-described enzyme of the present invention is isolated from the grown material.

The enzyme of the present invention can be prepared by growing a transformant under conditions suitable for its growth, expressing the nucleic acid of the present invention, and then preparing the product from the grown material.

In this case, the growth of a host cell is a general idea which includes not only culturing of the host cell but also administration of the host cell to a living body or the like and subsequent in vivo growth of the host cell. In addition, the grown material is a general idea which includes not only cultured host cell and culture supernatant but also, when the host cell is grown in vivo, discharged substances, secreted substances and the like from the living body.

For example, when COS-7 cell is selected as the host cell, it is possible to culture the transformant in vitro and to purify the substance of the present invention from its cultured material (transformant and culture supernatant after its alluring). As the method for isolating and purifying the enzyme of the present invention, it is possible to select an appropriate method optionally and conventionally, depending on the marker peptide. Particularly, when the above-described pFLAG-CMV-1 vector is used, the enzyme of the present invention is obtained as a fusion protein with FLAG peptide, so that it is possible to isolate and purify the enzyme of the present invention from the substance of the present invention by a method such as affinity purification, for example, using an anti-FLAG antibody (e.g., M1, etc.). When a resin or the like to which an anti-FLAG antibody is bound is used, it is possible to easily isolate and purify the protein from cultured materials of the host cell (culture supernatant, extracts of the host cell, etc.), and it is also possible to use the resin as an enzyme suspension by directly suspending it in a buffer or the like.

(6) Synthesis Method of the Present Invention (a) Synthesis Method 1 of the Present Invention The synthesis method 1 of the present invention is a method for synthesizing a sugar chain having a structure represented by the following formula (2), characterized in that the enzyme of the present invention is allowed to act upon a GalNAc acceptor having a structure represented by the following formula (1) and a GalNAc donor to thereby transfer a GalNAc residue from the GalNAc donor to the GalNAc acceptor:

$$(\text{GlcUA-GalNAc})_n\text{-(GlcUA)}_m \quad (1)$$

$$\text{GalNAc-(GlcUA-GalNAc)}_n\text{-(GlcUA)}_m \quad (2)$$

In formulae (1) and (2), GalNAc represents an N-acetyl-D-galactosamine residue, GlcUA represents a D-glucuronic acid residue; n is an integer of 1 or more; m is 1 or 0; and—represents a glycoside bond.

According to the synthesis method 1 of the present invention, the GalNAc acceptor is not particularly limited, so long as it has a sugar chain of the above-described formula (1) as a subject to which the GalNAc residue is transferred, GlcUA transferring enzyme activity and it may be a compound in which a sugar chain, a protein, a lipid, a synthetic high molecular weight compound or the like is further bound to its non-reducing end.

When the GalNAc residue is transferred from a GalNAc donor by allowing the enzyme of the present invention to act upon the GalNAc acceptor of the above-described formula (1), a compound having a structure represented by the above-described formula (2) is obtained.

The chondroitin backbone consists of a structure in which a disaccharide obtained by the GlcUA residue and the GalNAc residue though a β1,3-glycoside bond is further bound through a β1,4-glycoside bond, and it is preferred that the GalNAc residue can be bound to such a sugar chain also in the case of the synthesis method 1 of the present invention. That is, it is more preferable that the GalNAc acceptor having the structure of the above-described formula (1) has a structure of the following formula (1'):

$$(4\text{GlcUA}\beta 1\text{-}3\text{GalNAc}\beta 1)_n\text{-}4(\text{GlcUA})_m \quad (1')$$

In formula (1'), GlcUA, GalNAc and—have the same meanings as those described in the above-described formula (1); β represents a β bond; and the numerals indicate binding positions of adjoining sugar residues (positions on which a glycoside bond is present).

A product comprising a structure of the following formula (2') is preferably obtained by transferring a GalNAc residue to formula (1') by the enzyme of the present invention. This is bemuse the activity of binding the GalNAc residue to the GlcUA residue through a β1,4 glycoside bond is necessary for the synthesis of the chondroitin backbone:

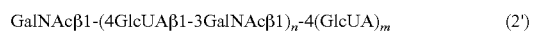

$$\text{GalNAc}\beta 1\text{-}(4\text{GlcUA}\beta 1\text{-}3\text{GalNAc}\beta 1)_n\text{-}4(\text{GlcUA})_m \quad (2')$$

In formula (2'), GlcUA, GalNAc and—have the same meanings as those described in the above-described formula (2); β represents a β bond; and the numerals indicate binding positions of adjoining sugar residues (positions on which a glycoside bond is present).

According to the synthesis method 1 of the present invention, the GalNAc residue is transferred from a GalNAc donor to a GalNAc actor. The enzyme of the present invention used in the synthesis method 1 of the present invention is preferably one which transfers the GalNAc residue from the above-described GalNAc donor to the above-described GalNAc acceptor through a β1,4 glycoside bond. This is because the GalNAc residue is bound to the chondroitin backbone through a β1,4 glycoside bond.

The transfer reaction of the GalNAc residue from a GalNAc donor to a GalNAc acceptor in the synthesis method of the present invention is preferably carried out within the range of the optimum reaction pH and optimum reaction temperature of the enzyme of the present invention. For example, the pH is preferably from 5.0 to 9.0, more preferably from 5.5 to 8.0, and most preferably from 6.0 to 7.5. In order to maintain such conditions, the above-described transfer reaction is preferably carried out in a buffer. Examples of the buffer include an acetate buffer, an MES buffer, a hydroxymethylaminoethane-hydrochloric acid buffer (hereinafter sometimes simply referred to as "Tris-HCl buffer"), a sodium phosphate buffer and the like, and any one of them can be used. However, MES is most preferred because of its potent activity to keep the pH stable throughout the most preferable pH range (pH 6.0 to 7.5) according to the synthesis method of the present invention. Although the concentration of buffer agents of the buffer is not particularly limited, a range of from 10 to 200 mol/l, from 20 to 100 mmol/l as a preferred range, can be exemplified.

In addition, it is preferred that a divalent metal cation, more preferably a manganese ion, a cobalt ion or the like, most preferably a manganese ion, is contained in this buffer for the purpose of accelerating the enzyme activity. The metal cation may be added in the form of a salt to the buffer. Examples of the salt include a halide of the above-described metal cation such as manganese chloride.

The temperature at the time of the reaction is, for example, from 20 to 45° C., preferably from 24 to 40° C., and more preferably from 36 to 37° C.

The enzyme of the present invention can be used in the synthesis of the sugar chains described in the above-described formula (2) and formula (2'), and its use for transferring the GalNAc residue which is present at the non-reducing end of a sugar chain having a structure of formula (2) or formula (2') is regarded as the use of the present invention.

(b) Synthesis Method 2 of the Present Invention

The synthesis method 2 of the present invention is a method for synthesizing a sugar chain having a structure represented by the following formula (4), characterized in that the enzyme of the present invention is allowed to act upon a GlcUA acceptor having a structure represented by the following formula (3) and a GlcUA donor to thereby transfer a GlcUA residue from the GlcUA donor to the GlcUA acceptor:

(3)

(4)

In formulae (3) and (4), GalNAc represents an N-acetyl-D-galactosamine residue; GlcUA represents a D-glucuronic acid residue; n is an integer of 1 or more; m is 1 or 0; and—represents a glycoside bond.

According to the synthesis method 2 of the present invention, the GlcUA acceptor is not particularly limited, so long as it has a sugar chain of the above-described formula (3) as a subject to which a GlcUA residue is transferred, and it may be a compound having a structure in which a sugar chain, a protein, a lipid, a synthetic high molecular weight compound or the like is further bound to its non-reducing end.

When the GlcUA residue is transferred from a GlcUA donor by allowing the enzyme of the present invention to act upon the GlcUA acceptor of the above-described formula (3), a compound having a structure represented by the above-described formula (4) is obtained.

The chondroitin backbone consists of a structure in which a disaccharide obtained by the GlcUA residue and the GalNAc residue through a β1,3 glycoside bond is further bound through a β1,4 glycoside bond, and it is preferable that GlcUA residue can be bound to such a sugar chain also in the synthesis method 2 of the present invention similar to the case of the synthesis method 1 of the present invention. That is, more preferably, the GlcUA acceptor having the structure of the above-described formula (3) has a structure of the following formula (3'):

(3')

In formula (3'), GlcUA, GalNAc and—have the same meanings as those described in the above-described formula (3); β represents a β bond; and the numerals indicate binding positions of adjoining sugar residues (positions on which a glycoside bond is present).

A product comprising a structure of the following formula (4') is preferably obtained by transferring the GlcUA residue to formula (3') by the enzyme of the present invention. This is because activity of binding the GlcUA residue to the GalNAc residue through a β1,3 glycoside bond is necessary for the synthesis of the chondroitin backbone:

(4')

In formulae (3') and (4'), GlcUA, GalNAc and—have the same meanings as those described in the above-described formulae (1) and (2); β represents a β bond; and the numerals indicate binding positions of adjoining sugar residues (positions on which a glycoside bond is present).

According to the synthesis method 2 of the present invention, the GlcUA residue is transferred from a GlcUA donor to a GlcUA acceptor. The enzyme of the present invention used in the synthesis method 2 of the present invention is preferably one which transfers the GlcUA residue from the above-described GlcUA donor to the above-described GlcUA acceptor through a β1,3 glycoside bond. This is because the GlcUA residue is bound to the chondroitin backbone through a β1,3 glycoside bond.

The transfer reaction of the GlcUA residue from a GlcUA donor to a GlcUA acceptor in the synthesis method of the present invention is preferably carried out at the optimum reaction pH and optimum reaction temperature of the enzyme of the present invention. For example, the pH is preferably from 4.0 to 8.0, more preferably from 4.5 to 7.0, still more preferably from 5.7 to 6.7, and most preferably from 6.0 to 6.5. In order to maintain such conditions, the above-described transfer reaction is preferably carried out in a buffer. Examples of the buffer include an acetate buffer MES, a Tris-HCl buffer, a sodium phosphate buffer and the like, and any one of them can be used. However, MES is preferred because of its potent activity to keep the pH stable throughout the most preferred pH range (pH 6.0 to 5.5) according to the synthesis method of the present invention. This is because the pH can be kept more stably since pH 6.0 to 6.5 is a center range among the buffering region. Although the concentration of buffer agents of the buffer is not particularly limited, a range of from 10 to 200 mol/l, from 20 to 100 mmol/l as a preferred range, can be exemplified.

In addition, a divalent metal cation, more preferably a manganese ion, a cobalt ion or the like, and most preferably a manganese ion, is contained in this buffer for the purpose of accelerating the enzyme activity. The metal cation may be added in the form of a salt to the buffer. Examples of the sat include a halide of the above-described metal cation such as manganese chloride.

The temperature at the time of the reaction is, for example, from 20 to 45° C., preferably from 24 to 40° C., and most preferably from 36 to 37° C.

The enzyme of the present invention can be used in the synthesis of the sugar chains described in the above-described formula (4) and formula (4'), and its use for transferring GlcUA residue existing at the non-reducing end of a sugar chain having a structure of formula (4) or formula (4') is regarded as the use of the present invention.

EXAMPLE 1

Preparation of Enzyme of the Present Invention (1) Cloning of cDNA and Construction of Expression Vector BLAST search was carried out by using an amino acid sequence of chondroitin sulfate-glucuronic acid transferase (CSGlcA-T) (the amino acid sequence encoded by GenBank accession No. AB037823) as the query. As a result, EST (GenBank accession No. NM-018590) was found. However, since this sequence was incomplete, ORF was examined from a genomic data base by GenScan (Stanford University, USA). As a result, the nucleotide sequence represented by SEQ ID NO:1 (the encoded amino acid sequence in SEQ ID NO:2) was found. It was confirmed by RT-PCR using Marathon-Ready cDNA (manufactured by Clontech) as the template that a gene consisting of the nucleotide sequence represented by SEQ ID NO:1 was expressed at least in the human brain. In order to carry out cloning of the soluble region of this gene except for a region including the transmembrane region (a region consisting of amino acid numbers 1 to 96 of SEQ ID NO:2), PCR was carried out in accordance with a usual method by using two primers represented by SEQ ID NO:3 and SEQ ID NO:4. As the template cDNA use, Marathon-Ready cDNA human brain (manufactured by Clontech) was used. The thus amplified band of about 2 kb was digested with EcoRI and BamHI in accordance with a usual method and inserted into EcoRI and BamHI sites of an expression vector for mammal cell, pFLAG-CMV-1 (manufactured by Sigma), to thereby obtain K11-FLAG-CMV-1. As a result that the nucleotide sequence of the thus obtained vector was confirmed, it was confirmed that a DNA fragment consisting of nucleotide numbers 287 to 2328 of the nucleotide sequence represented by SEQ ID NO:1 was inserted (2) Preparation of the Enzyme of the Present Invention Using 15 μg of the K11-FLAG-CMV-1 and TransFast (manufactured by Promega) in accordance with the protocol, a gene was introduced into COS-7 cell which had been cultured in a 100 mm culture dish to reach a 70% confluent stage. The supernatant after culturing for 3 days was recovered and filtered through a 0.22 μm filter, and then 100 μl of Anti-FLAG M2-Agarose Affinity Gel (manufactured by Sigma) was added to 10 ml of the supernatant and mixed on a roller at 4° C. overnight. After the reaction, the gel was washed three times with 50 mmol/l Tris-HC, pH 7.4/20% glycerol, and then excess wash water was removed by using a syringe with a 27 G injection needle. This gel was suspended in 50 mmol/l Tris-HCl, pH 7.4/20% glycerol/10 mmol/l phenylmethylsulfonyl fluoride/1 μg/ml leupeptin/1 μg/ml pepstatin to give a concentration of 50% (v/v), followed by centrifugation, and then the supernatant was discarded to obtain an enzyme-adsorbed gel suspension.

EXAMPLE 2

Elongation of Chondroitin Backbone Using the Enzyme of the Present Invention (1) Preparation of Chondroitin/Chondroitin Sulfate Odd-Numbered Saccharide Chondroitin (shark-derived chondroitin sulfate was chemically de-sulfated: manufactured by Seikagaku Corporation) and chondroitin sulfate (cartilage derived from shark: manufactured by Seikagaku Corporation) were limitedly digested with bovine testicle hyaluronidase (manufactured by Sigma), and then the reaction solution was kept at 100° C. for 10 minutes to heat-inactivate the enzyme. This reaction solution was applied to Superdex 30 column (60× 1.6 cm: manufactured by Amersham Bioscience, chromatography conditions; mobile phase: 0.2 mol/l $NH_4HCO_3$, flow rate: 2 ml/minute), and the eluates were fractionated at 2 ml while monitoring at an absorbance of 225 nm to pool fractions corresponding to deca-saccharides. Each fraction was desalted by using PD10 column (manufactured by Amersham Bioscience), and uronic acid was determined by the carbazole-sulfuric acid method in accordance with the usual method, followed by freeze-drying. The freeze-dried samples were dissolved in distilled water to give a concentration of 1 mmol/l and used as even-numbered oligosaccharide samples (the chondroitin-derived deca-saccharide is referred to as "CH10", and the chondroitin sulfate-derived deca-saccharide is referred to as "CS10").

To 50 mmol/l MES buffer (pH 6.5) containing 10 mmol/l $MnCl_2$ and 171 μmol of ATP sodium salt, 10 μl of the enzyme-adsorbed gel suspension, 10 nmol of a substance to be tested (chondroitin (CHEL), chondroitin sulfate (CSEL), CH10 or CS10) and 0.036 nmol of [$^3$H]UDP-GalNAc were added, and the total volume was adjusted to 30 μl. The enzyme reaction was carried out at 37° C. for 1 hour, and then the reaction was stopped by keeping the reaction solution at 100° C. for 1 minute to inactivate the enzyme.

Each reaction solution was filtered through a microfilter of 0.22 μm in pore size (manufactured by Millipore) and then separated by Superdex peptide column (30×1.0 cm: manufactured by Amersham Bioscience, chromatography conditions; mobile phase: 0.2 mol/l NaCl, flow rate: 0.5 ml/minute), and the eluates were fractionated at 0.5 ml to measure the radioactivity by using a scintillation counter (FIG. 1). As a result, strong GalNAc transferring activity was observed when CHEL (18th fraction), CH10 (23rd fraction) and CS10 (23rd fraction) were used as the GalNAc acceptor substrates, while weak GalNAc transferring activity was observed for CSEL (16th fraction). The 22nd and 23rd fractions of the reaction products obtained from CH10 and CS10 were fractions showing molecular weights of eluted undeca-saccharides. The undeca-saccharide obtained from CH10 is referred to as "CH11", and the undeca-saccharide obtained from CS10 is referred to as "CS11".

The 21st to 25th fractions of CS11 were pooled and desalted by using PD10 column. The thus obtained sample was divided into two equal parts and freeze-dried. One of the bisected parts was dissolved in 100 μl of 0.1 mol/l Tris-HCl buffer (pH 7.4) containing 30 mmol/l sodium acetate (CS11A), and another was digested with chondroitinase ACII (100 mU of chondroitinase ACII (manufactured by Seikagaku Corporation) was dissolved in 100 μl of CS11 fraction, followed by enzymatic digestion at 37° C. for 10 hours and then heating to inactivate the enzyme: CS11B).

Figure 2:
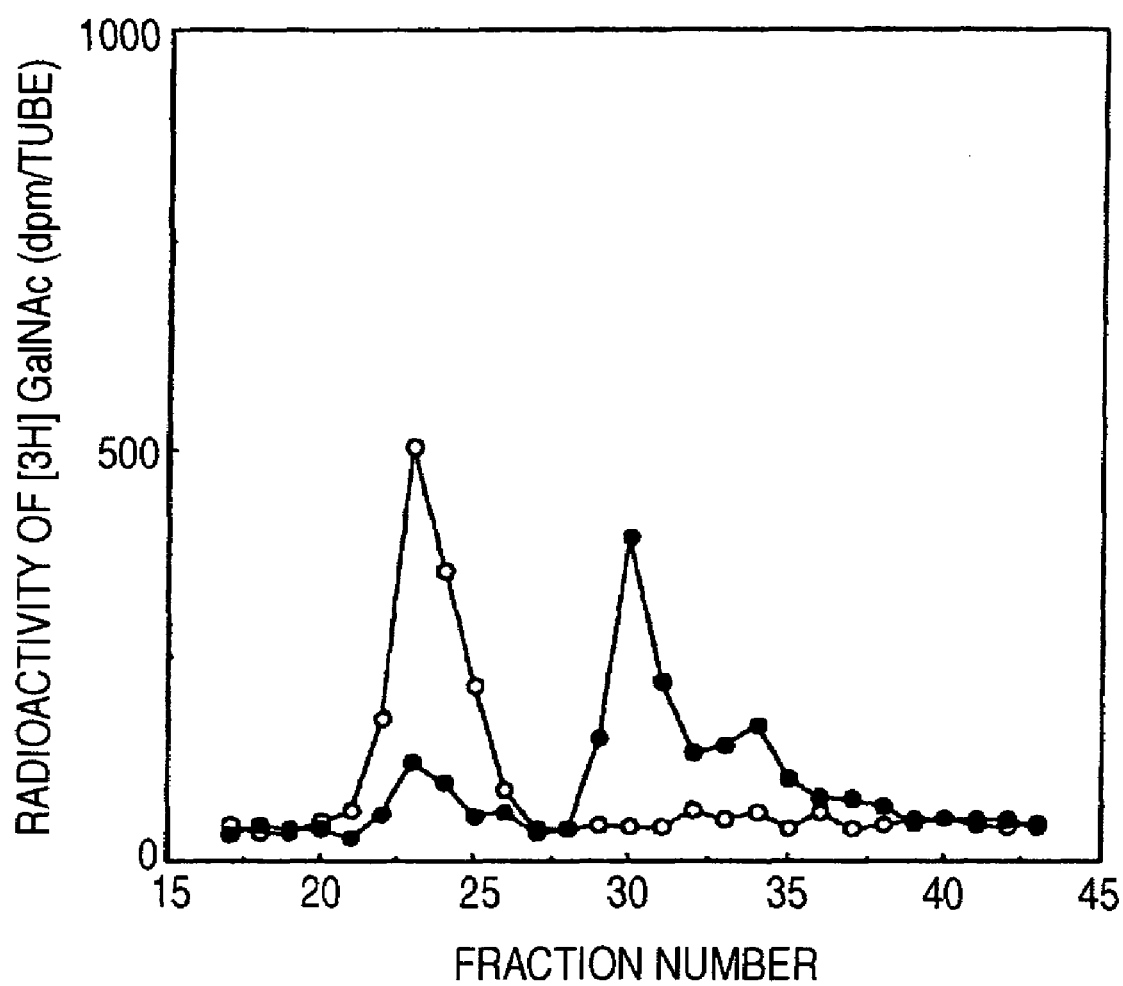
FIG. 2 is a graph showing a chromatography chart of a undeca-saccharide prepared by the GalNAc transferring activity of the enzyme of the present invention and its chondroitinase ACII digests. Open circles represent a chart of chondroitinase ACII-undigested undeca-saccharide, and closed circles represent a chart of digested product after chondroitinase ACII digestion.

CS11A and CS11B were filtered through a microfilter of 0.22 μm in pore size (manufactured by Millipore) and then separated by Superdex peptide column (30×10 mm: manufactured by Amersham Bioscience, chromatography conditions; mobile phase: 0.2 mol/l NaCl, flow rate: 0.5 ml/minute) and the eluates were fractionated at 0.5 ml, and when the radioactivity was measured by using a scintillation counter, the radioactivity peak was shifted to the trisaccharide fraction in CS11B (FIG. 2). It was considered from this result that the enzyme of the present invention can prepare a undeca-saccharide by transferring GalNAc through a β1,4 bond to GlcUA of the non-reducing end of the chondroitin sulfate-derived deca-saccharide.

(2) Preparation of Chondroitin/Chondroitin Sulfate Even-Numbered Saccharides

Chondroitin (shark-derived chondroitin sulfate was chemically de-sulfated: manufactured by Seikagaku Corporation) and chondroitin sulfate (derived from shark cartilage: manufactured by Seikagaku Corporation) were limitedly digested with bovine testicle hyaluronidase (manufactured by Sigma), and then the reaction solution was kept at 100° C. for 10 minutes to heat-inactivate the enzyme. This reaction solution was centrifuged at 10,000×g for 10 minutes, and the supernatant was recovered and further digested with a bovine liver-derived β-glucuronidase (manufactured by Sigma). The enzyme reaction was stopped by keeping the reaction solution at 100° C. for 10 minutes. This reaction solution was applied to Superdex 30 column (60×1.6 cm: manufactured by Amersham Bioscience, chromatography conditions; mobile phase: 0.2 mol/l $NH_4HCO_3$, flow rate: 2 ml/minute), and the eluates were fractionated at 2 ml while monitoring at an absorbance of 225 nm to pool fractions corresponding to undeca-saccharides. Each fraction was desalted by using PD10 column (manufactured by Amersham Bioscience), and uronic acid was determined by the carbazole-sulfuric acid method in accordance with the usual method, followed by freeze-drying. The freeze-dried samples were dissolved in distilled water to give a concentration of 1 mmol/l and used as odd-numbered oligosaccharide samples (the chondroitin-derived undeca-saccharide: "CH11", the chondroitin sulfate-derived undeca-saccharide: "CS11").

Also, chondroitin (shark chondroitin sulfate was chemically de-sulfated: manufactured by Seikagaku Corporation) and chondroitin sulfate (derived from shark cartilage: manufactured by Seikagaku Corporation) were digested with bovine liver-derived β-glucuronidase (manufactured by Sigma) to prepare samples (referred to as "CHOL" and "CSOL", respectively).

To 50 mmol/l acetate buffer (pH 5.6) containing 10 nmol/l of $MnCl_2$, 10 μl of the enzyme-adsorbed gel suspension, 1 nmol of a substance to be tested (CHOL, CHOL, CH11 or CS11) and 0.432 nmol of [$^{14}$C]UDP-GlcUA were added, and the total volume was adjusted to 30 μl. The enzyme reaction was carried out at 37° C. for 1 hour, and then the reaction was stopped by keeping the reaction solution at 100° C. for 1 minute to inactivate the enzyme.

Figure 3:
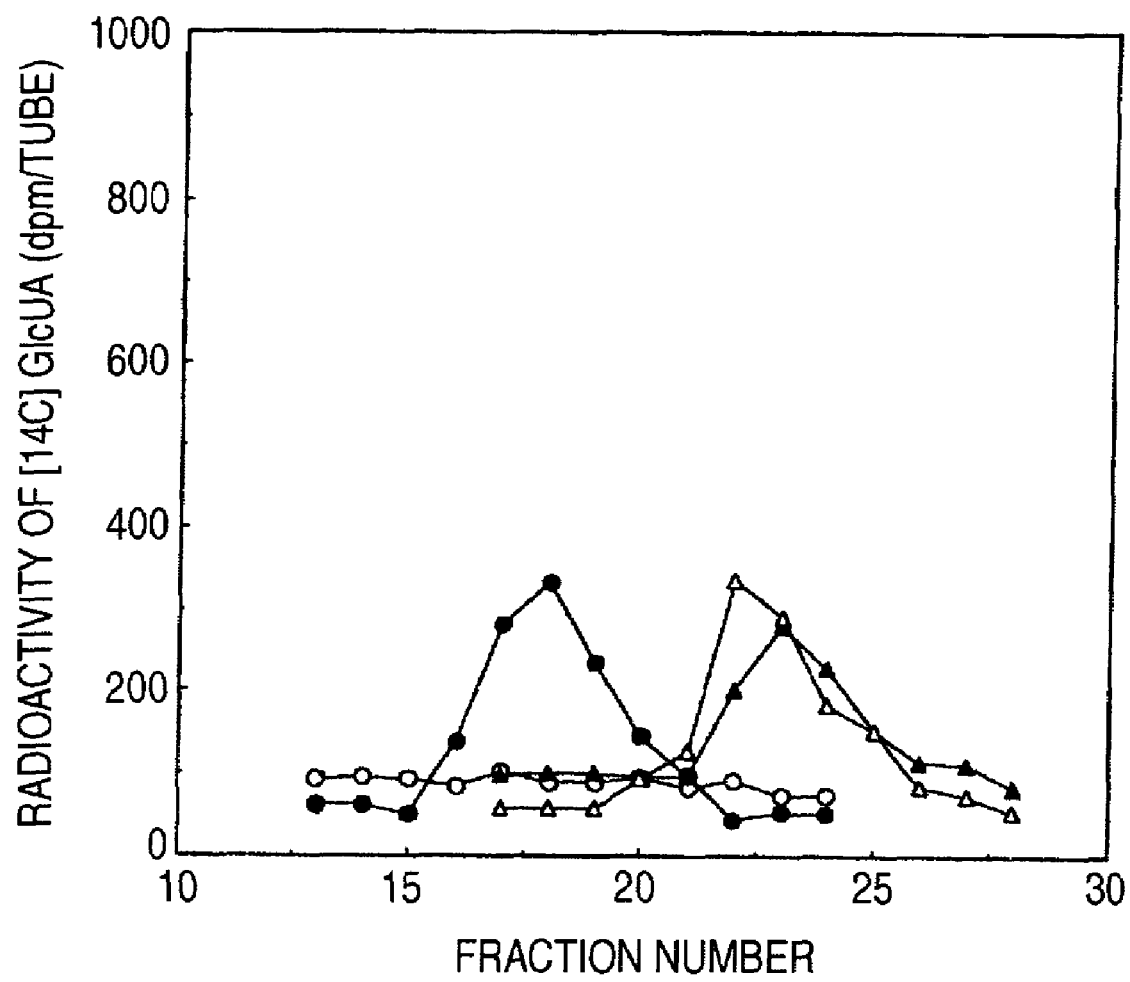
FIG. 3 is a graph showing a chromatography chart showing synthesis of even-numbered saccharides by the GlcUA transfer activity of the enzyme of the present invention. Open circles represent a chart showing the GlcUA transfer activity upon chondroitin sulfate, closed circles represent a chart showing the GlcUA transfer activity upon chondroitin, open triangles represent a chart showing the GlcUA transfer activity upon chondroitin sulfite undeca-saccharide, and closed triangles represent a chart showing the GlcUA transfer activity upon chondroitin undeca-saccharide.

Each reaction solution was filtered through a microfilter of 0.22 μm in pore size (manufactured by Millipore) and then separated by Superdex peptide column (30×1.0 cm: manufactured by Amersham Bioscience, chromatography conditions; mobile phase; 0.2 mol/NaCl, flow rate: 0.5 ml/minute), and the eluates were fractionated at 0.5 ml to measure the radioactivity by using a scintillation counter (FIG. 3). As a result, strong GlcUA transferring activity was observed when CHOL (18th fraction), CH11 (23rd fraction) and CS11 (22nd fraction) were used as the GlcUA acceptor substrates while the GlcUA transferring activity was not observed for CHOL. The 22nd and 23rd fractions of the reaction products obtained from CH11 and CS11 were fractions showing molecular weights of eluted dodeca-saccharides. The dodeca-saccharide obtained from CH11 is referred to as "CH12", and the dodeca-saccharide obtained from CS11 is referred to as "CS12".

The 21st to 25th fractions of CS12 were pooled and desalted by using PD10 column. The thus obtained sample was divide into two equal parts and freeze-dried. One of the bisected parts was dissolved in 100 μl of 0.1 mol/l Tris-HCl buffer (pH 7.4) containing 30 mmol/l sodium acetate (CS12A), and another was digested with chondroitinase ACII (100 mU of chondroitinase ACII (manufactured by Seikagaku Corporation) was dissolved in 100 μl of CS11 fraction, followed by enzymatic digestion at 37° C. for 10 hours and then heating to inactivate the enzyme: CS12B).

Figure 4:
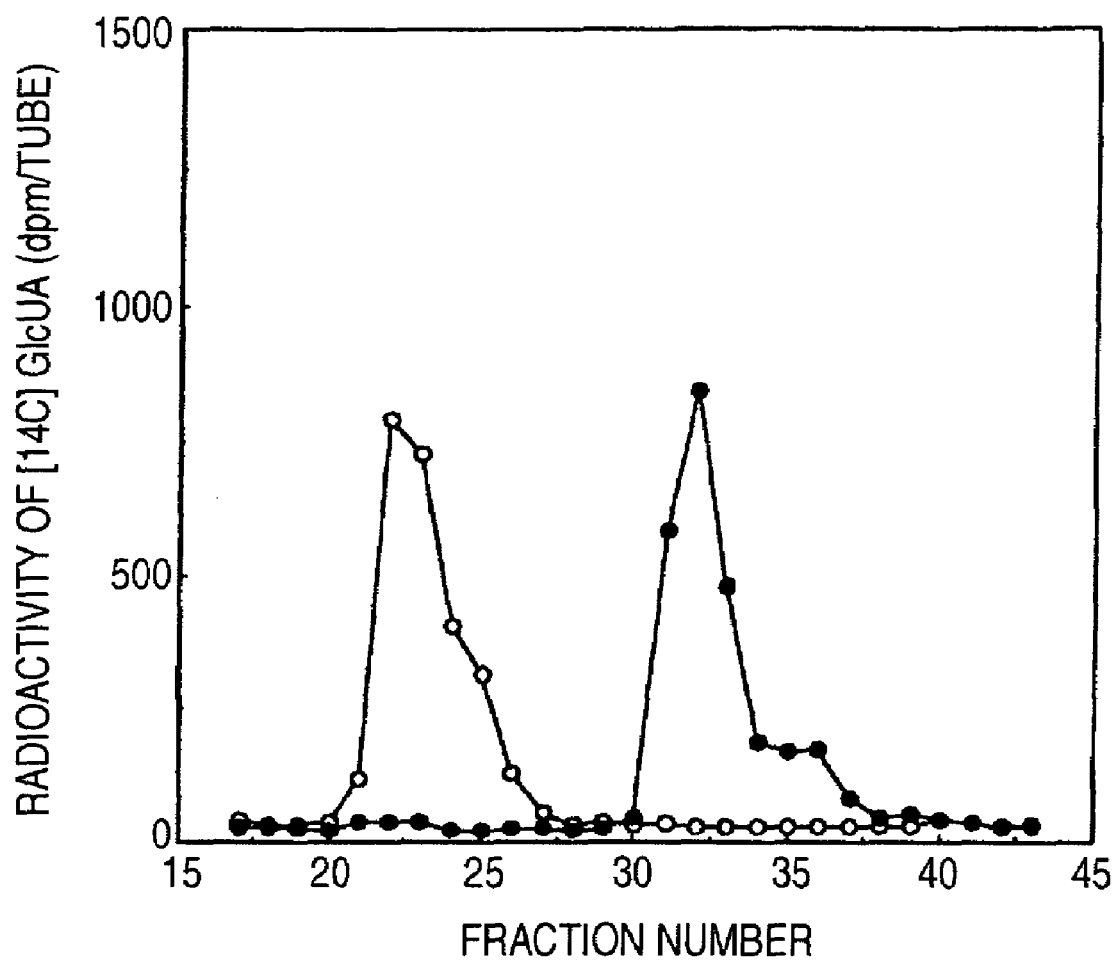
FIG. 4 is a graph showing a chromatography chart of a dodeca-saccharide prepared by the GlcUA transferring activity of the enzyme of the present invention and its chondroitinase ACII digests. Open circles represent a chart of chondroitinase ACII-undigested dodeca-saccharide, and closed circles represent a chart of digested product after chondroitinase ACII digestion.

CS12A and CS12B were filtered through a microfilter of 0.22 μm in pore size (manufactured by Millipore) and then separated by Superdex peptide column (30×1.0 cm: manufactured by Amersham Bioscience, chromatography conditions; mobile phase: 0.2 mol/l NaCl, flow rate: 0.5 ml/minute) and the eluates were fractionated at 0.5 ml, and when the radioactivity was measured by using a scintillation counter, the radioactivity peak was shifted to the disaccharide fraction in CS12B (FIG. 4). It was found from this result that the enzyme of the present invention can prepare a dodeca-saccharide by transferring GlcUA through a β1,3 bond to the chondroitin sulfate-derived undeca-saccharide.

EXAMPLE 3

The GlcUA and GalNAc transferring activities of the enzyme of the present invention of Example 2 were checked for their optimum pH by changing the pH of buffers. An acetate buffer, an MES buffer, an imidazole buffer and a Tris-HCl buffer were used at a final concentration of 50 mmol/l for each buffer.

Figure 5:
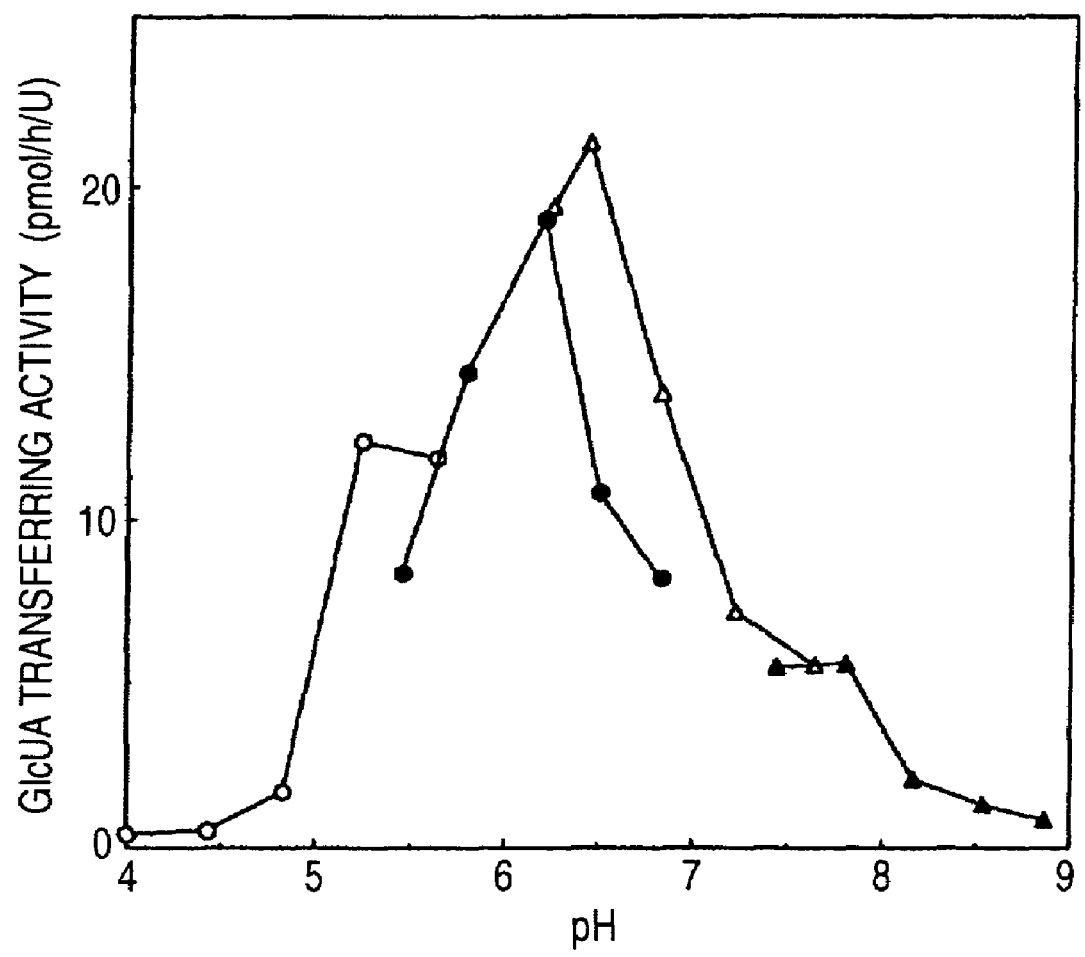
FIG. 5 is a graph showing optimum pH of the GlcUA transferring activity of the enzyme of the present invention. Open circles represent the optimum pH using an acetate buffer, closed circles represent the optimum pH using an MES buffer, open triangles represent the optimum pH using an imidazole buffer, and closed triangles represent the optimum pH using a Tris buffer.
Figure 6:
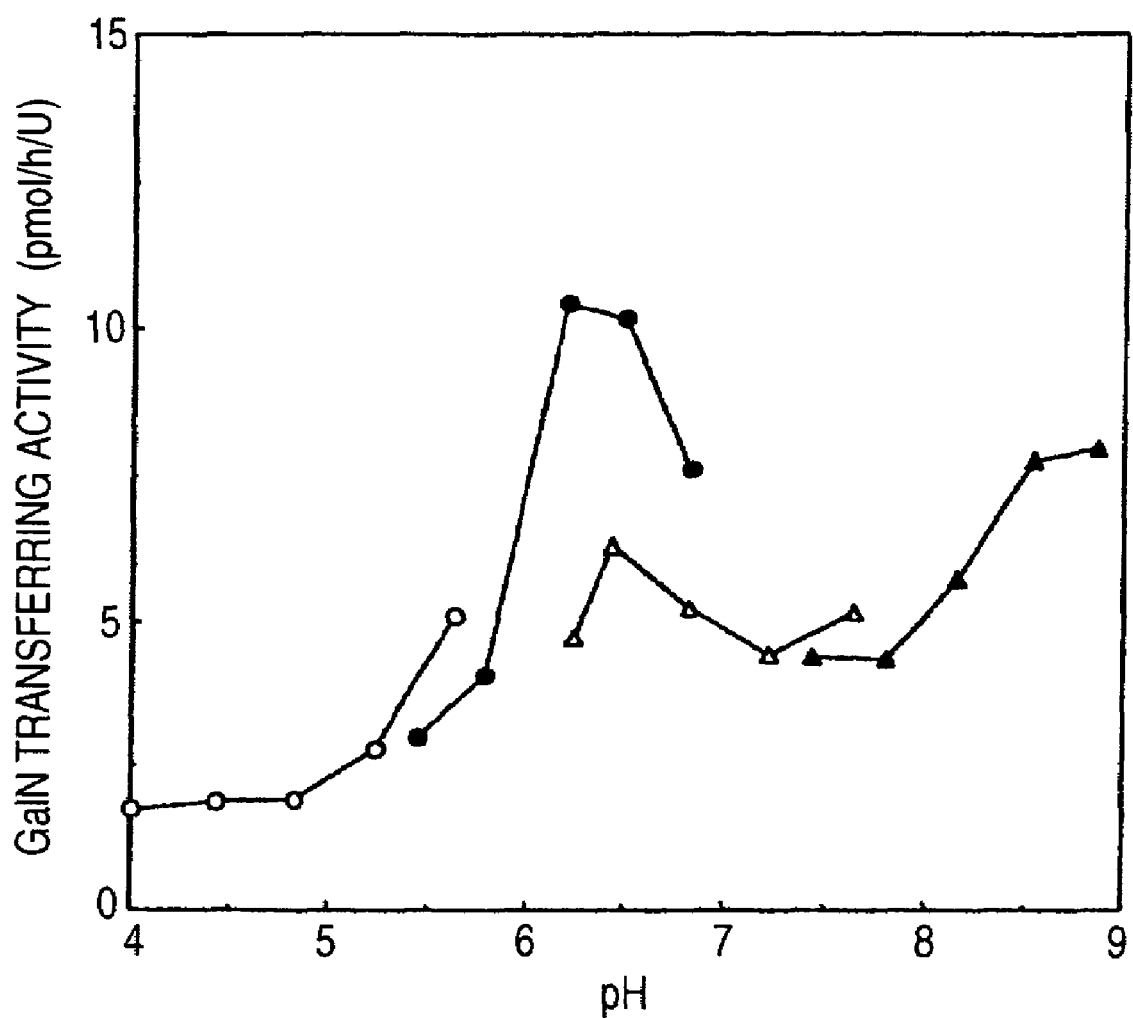
FIG. 6 is a graph showing optimum pH of the GalNAc transferring activity of the enzyme of the present invention. Open circles represent the optimum pH using an acetate buffer, closed circles represent the optimum pH using an MES buffer, open triangles represent the optimum pH using an imidazole buffer, and closed triangles represent the optimum pH using a Tris buffer.

As a result, it was found that the optimum pH of the GlcUA transferring activity was 6.0 to 6.5 (FIG. 5), and the optimum pH of the GalNAc transferring activity was 6.0 to 6.5 (FIG. 6).

EXAMPLE 4

Figure 7:
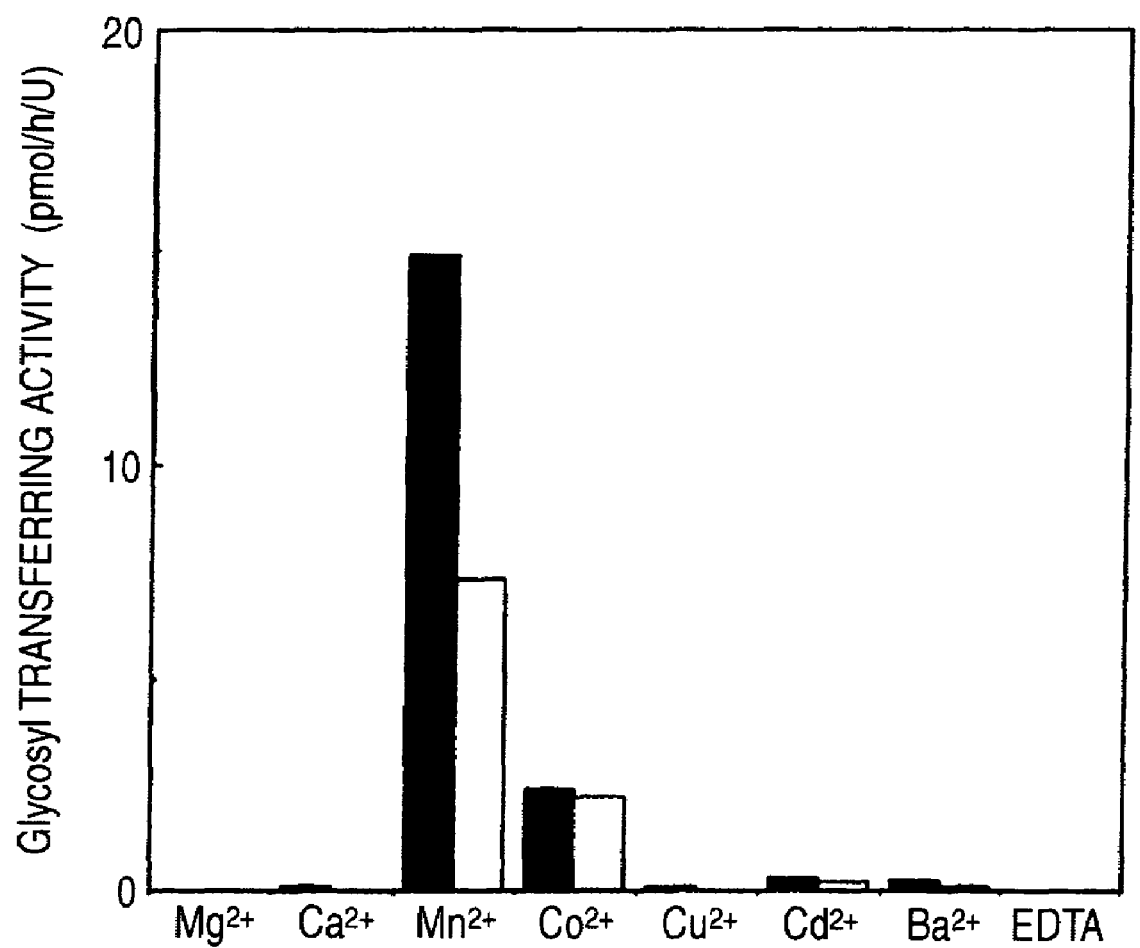
FIG. 7 is a graph showing influence of divalent cations upon the activities of the enzyme of the present invention. Open bars represent the GlcUA transferring activity, and closed bars represent the GalNAc transferring activity.

Under the measuring conditions for the GlcUA transferring activity and GalNAc transferring activity of the enzyme of the present invention of Example 2, the GlcUA transferring activity and GalNAc transferring activity were examined by adding 10 mmol/l ethylenediaminetetraacetic acid (EDTA) to the reaction system to find that the enzyme activities were completely lost (FIG. 7). Thus, it was found that the enzyme of the present invention requires a divalent cation for its activities.

Also, it was found that high enzyme activities were obtained when 10 mmol/l $CoCl_2$ was added to the reaction system instead of $MnCl_2$ (FIG. 7).

Figure 8:
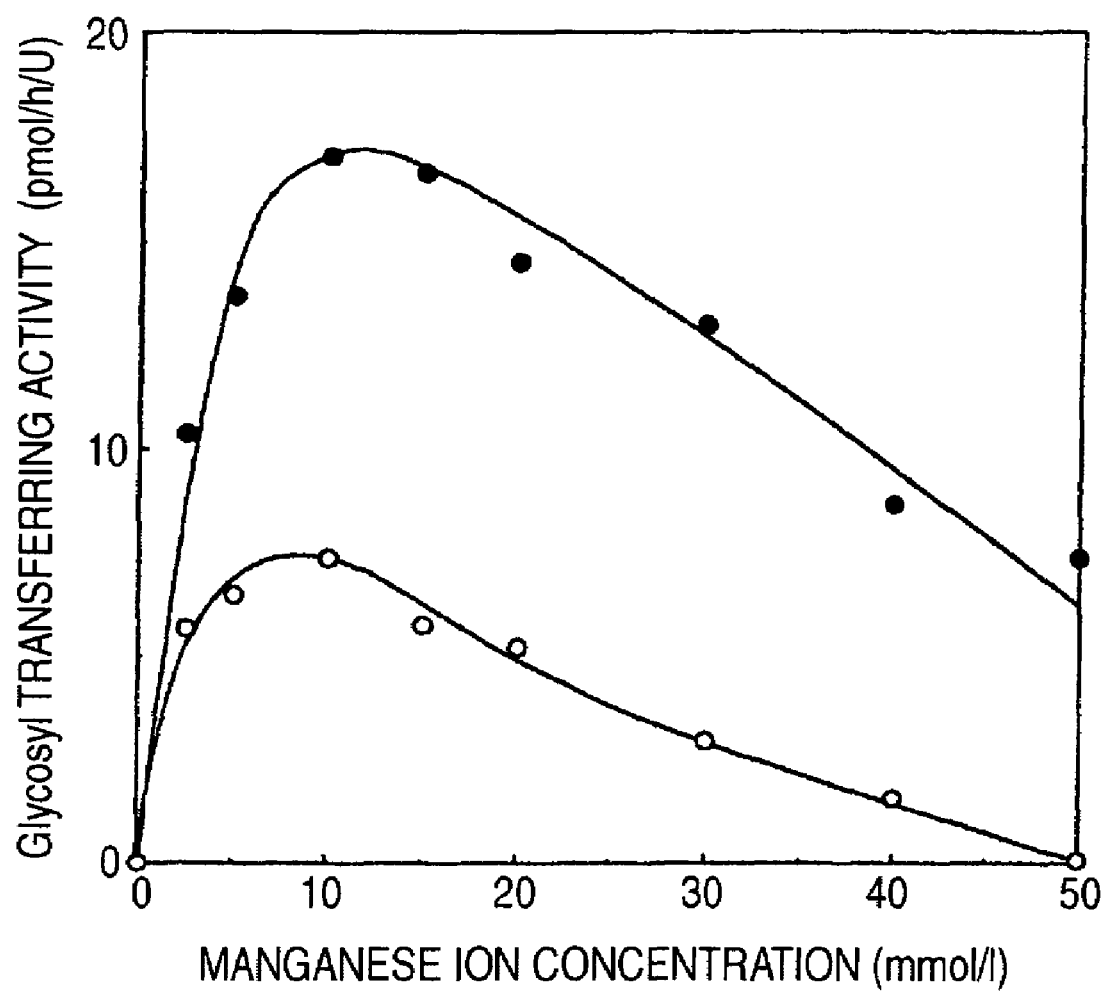
FIG. 8 is a graph showing influence of a manganese ion concentration upon the activities of the enzyme of the present invention. Open circles represent influence upon the GlcUA transferring activity of the enzyme of the present invention, and closed circles represent influence upon the GalNAc transferring activity of the enzyme of the present invention.

In addition, in order to examine influence of the concentration of a manganese ion upon activities of the enzyme of the present invention, the GlcUA transferring activity and GalNAc transferring activity were measured in the same manner by changing the final concentration of a manganese ion within the range of from 0 to 50 mmol/l under the reaction conditions of Example 2, which found that each of the activities has a requirement for an optimum manganese ion concentration at 10 mmol/l (FIG. 8).

EXAMPLE 5

Figure 9:
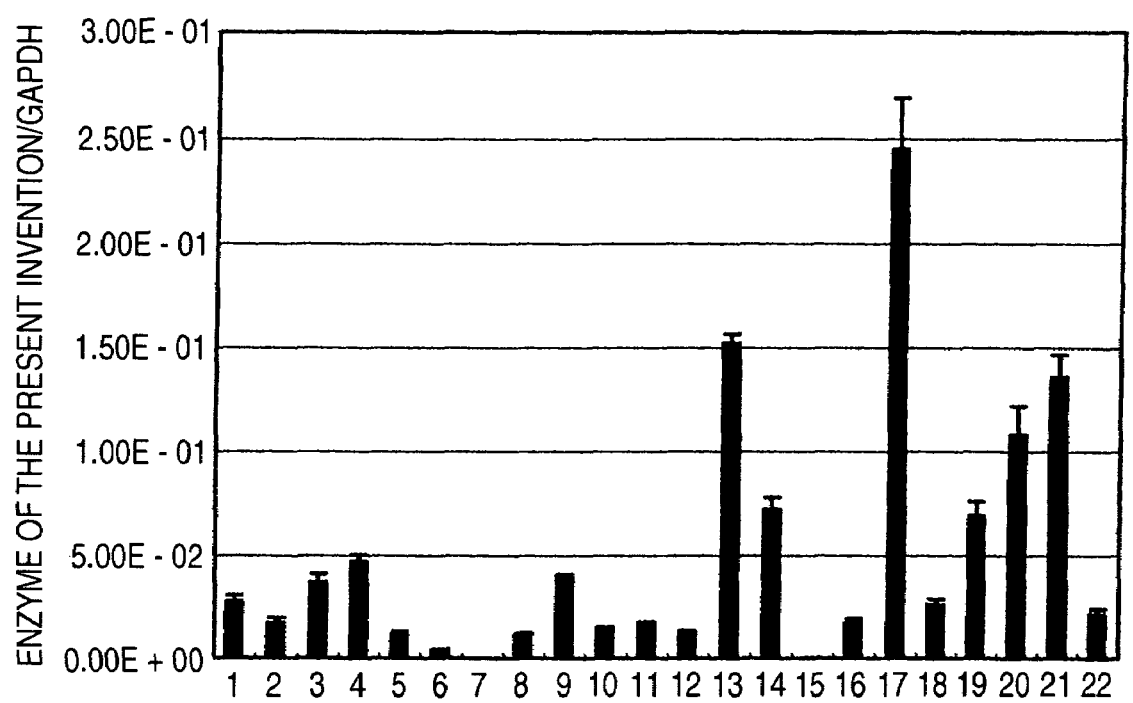
FIG. 9 is a graph showing determined values of the expression of the enzyme of the present invention in respective tissues of healthy person

Analysis of Expression Pattern of the Gene of the Present Invention in Human Tissues In order to analyze the expressed level of the gene of the present invention in various human tissues, a real time PCR method (RT-PCR) was used. Amplification and determination were carried out by using various types of Marathon-Ready cDNA (manufactured by Clontech) as the template, two primers (SEQ ID NO:5 and SEQ ID NO:6) and a probe (SEQ ID NO:7) in which a miner groove binder (manufactured by Applied Biosystems) was bound to the 3' end. As the standard gene, a plasmid pCR2.1 (manufactured by Invitrogen) containing glyceraldehyde triphosphate dehydrogenase (GAPDH) was used by making a dilution series and thereby preparing a calibration curve. In addition, ABI PRISM 7700 (manufactured by Applied Biosystems) was used in the RT-PCR (FIG. 9). The expression quantity in FIG. 9 indicates expressed levels in 1: trachea, 2: brain, 3: liver, 4: skeletal muscle, 5: uterus, 6: kidney, 7: heart, 8: fetal brain, 9: salivary gland, 10: cerebellum, 11: spinal cord, 12: fetal liver, 13: placenta, 14: testis, 15: prostate, 16: mammary gland, 17: pancreas, 18: adrenal gland, 19: thyroid, 20; stomach, 21; small intestines, and 22: colon.

As a result, it was found that the gene of the present invention is potently expressed in the placenta, testis, pancreas, thyroid, stomach and small intestines, particularly in the pancreas.

While the present invention has been described in detail and with reference to specific embodiments thereof, it will be apparent to one of skill in the art that various changes and modifications can be made therein without departing from the spirit and scope thereof. All references cited herein are incorporated in their entirety.

This application is based on Japanese application Nos. 2002-160854 and 2003-128343 filed on May 31, 2003 and May 6, 2003, respectively, the entire contents of which are incorporated hereinto by reference.

INDUSTRIAL APPLICABILITY

The present invention provides a human-derived novel chondroitin synthase, which is an enzyme for synthesizing a fundamental backbone of chondroitin and has both glucuronic acid transferase activity and N-acetylgalactosamine transferase activity.

Free Text of Sequence Listing

SEQ ID NO:3—Explanation of synthetic sequence: Synthetic DNA

SEQ ID NO:4—Explanation of synthetic sequence: Synthetic DNA

SEQ ID NO:5—Explanation of synthetic sequence: Synthetic DNA

SEQ ID NO:6—Explanation of synthetic sequence: Synthetic DNA

SEQ ID NO:7—Explanation of synthetic sequence: Synthetic DNA

The invention claimed is:

1. An isolated chondroitin synthase consisting of the amino acid sequence of SEQ ID NO:2, or consisting of amino acids 97 to 755 of SEQ ID NO:2, with the proviso that the chondroitin synthase may include one or more sugar chains covalently bound thereto.

2. An isolated polynucleotide encoding the chondroitin synthase according to claim 1.

3. An expression vector which comprises the polynucleotide according to claim 2.

4. The expression vector according to claim 3, which is capable of being expressed in a eucaryotic cell.

5. An isolated transformant which comprises the expression vector according to claim 3.

6. A process for producing a chondroitin synthase, which comprises growing the transformant according to claim 5 to produce and accumulate a chondroitin synthase as a grown material, and recovering the chondroitin synthase from the grown material.

7. A method for synthesizing a sugar chain having a structure represented by the following formula (2), which comprises allowing the chondroitin synthase according to claim 1 to act on an N-acetyl-D-galactosamine acceptor having a structure represented by the following formula (1) and an N-acetyl-D-galactosamine donor to thereby transfer an N-acetyl-D-galactosamine residue to the N-acetyl-D-galactosamine acceptor:

$$(GlcUA\text{-}GalNAc)_n\text{-}(GlcUA)_m \tag{1}$$

$$GalNAc\text{-}(GlcUA\text{-}GalNAc)_n\text{-}(GlcUA)_m \tag{2}$$

wherein, in formulae (1) and (2), GalNAc represents the N-acetyl-D-galactosamine residue; GlcUA represents a D-glucuronic acid residue; n is an integer of 1 or more; m is 1 or 0; and—represents a glycoside bond.

8. A method for synthesizing a sugar chain having a structure represented by the following formula (4), which comprises allowing the chondroitin synthase according to claim 1 to act upon a D-glucuronic acid acceptor having a structure represented by the following formula (3) and a D-glucuronic acid donor to thereby transfer a D-glucuronic acid residue to the D-glucuronic acid acceptor:

$$(GalNAc\text{-}GlcUA)_n\text{-}(GalNAc)_m \tag{3}$$

$$GlcUA\text{-}(GalNAc\text{-}GlcUA)_n\text{-}(GalNAc)_m \tag{4}$$

wherein, in formulae (3) and (4), GalNAc represents an N-acetyl-D-galactosamine residue; GlcUA represents the D-glucuronic acid residue; n is an integer of 1 or more; m is 1 or 0; and—represents a glycoside bond.

* * * * *